US007385203B2

(12) United States Patent
Nakayama et al.

(10) Patent No.: US 7,385,203 B2
(45) Date of Patent: Jun. 10, 2008

(54) CHARGED PARTICLE BEAM EXTRACTION SYSTEM AND METHOD

(75) Inventors: Takahide Nakayama, Nara (JP); Takayoshi Natori, Chiyoda (JP); Masaki Yanagisawa, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 285 days.

(21) Appl. No.: 11/146,074

(22) Filed: Jun. 7, 2005

(65) Prior Publication Data

US 2006/0273264 A1 Dec. 7, 2006

(51) Int. Cl.
*G01K 1/08* (2006.01)
*H01J 3/14* (2006.01)
*H01J 3/26* (2006.01)

(52) U.S. Cl. .................. 250/400; 250/492.3; 315/501; 315/505; 315/507

(58) Field of Classification Search ............. 250/492.3, 250/400; 315/501, 505, 507
See application file for complete search history.

(56) References Cited

U.S. PATENT DOCUMENTS

| 5,260,581 | A | 11/1993 | Lesyna et al. |
| 5,363,008 | A | 11/1994 | Hiramoto et al. |
| 2004/0118081 | A1 | 6/2004 | Reimoser et al. |
| 2006/0163496 | A1* | 7/2006 | Hiramoto et al. ........ 250/492.3 |

FOREIGN PATENT DOCUMENTS

| EP | 0 986 070 A1 | 3/2000 |
| EP | 1 454 654 A2 | 9/2004 |
| WO | WO 96/25201 | 8/1996 |
| WO | WO 2004/101070 A1 | 11/2004 |

OTHER PUBLICATIONS

W.T.Chu, B.A.Ludewigt and T.R.Renner, Review of Scientific Instruments vol. 64, No. 8, Aug. 1993, pp. 2055 to 2122.*
"Review of Scientific Instruments," vol. 64, No. 8, pp. 2074-2084, Aug. 1993.

* cited by examiner

*Primary Examiner*—Jack I. Berman
*Assistant Examiner*—Meenakshi S Sahu
(74) *Attorney, Agent, or Firm*—Dickstein Shapiro LLP

(57) ABSTRACT

A charged particle beam extraction system and method capable of ensuring higher safety when extraction of an ion beam is on/off-controlled during irradiation of the ion beam for treatment. The charged particle beam extraction system comprises a charged particle beam generator including a synchrotron, a range modulation wheel (RMW) for forming a Bragg peak width of a charged particle beam extracted from the charged particle beam generator, a gate signal generator for controlling start and stop of extraction of the charged particle beam from the charged particle beam generator in accordance with a rotational angle of the RMW, and an irradiation control/determination section for determining whether the start and stop of extraction of the charged particle beam is controlled at desired timing by the gate signal generator.

25 Claims, 16 Drawing Sheets

FIG. 9

| IRRADI-ATION FIELD SIZE | RANGE | INCIDENT Eg | SC1 THICK-NESS | SOBP WIDTH | SC2 TYPE | RS THICKNESS | BC APERTURE SIZE |
|---|---|---|---|---|---|---|---|
| φ 20[cm] | 40[mm] ... 90[mm] | 100[MeV] | 2[mm] | 1-1 | 1-1 | 50[mm] ... 0[mm] | φ 20[cm] |
| | 90[mm] ... 150[mm] | 150[MeV] | 4[mm] | 1-2 | 1-2 | 60[mm] ... 0[mm] | |
| | 150[mm] ... | 200[MeV] | 7[mm] | 1-3 | | 0[mm] | |
| | | 250[MeV] | 10[mm] | 1-4 | | 0[mm] | |
| φ 6[cm] | 40[mm] ... 90[mm] | 100[MeV] | 1[mm] | 2-1 | 2-1 | 50[mm] ... 0[mm] | φ 6[cm] |
| | 90[mm] ... 150[mm] | 150[MeV] | 2[mm] | 2-2 | 2-2 | 60[mm] ... 0[mm] | |
| | 150[mm] ... | 200[MeV] | 3.5[mm] | 2-3 | | 0[mm] | |
| | | 250[MeV] | 5[mm] | 2-4 | | 0[mm] | |

CHARGED PARTICLE BEAM EXTRACTION SYSTEM AND METHOD

BACKGROUND OF THE INVENTION

1. Field of the Invention

The present invention relates to a charged particle beam extraction system and method for irradiating a charged particle beam, e.g., a proton or carbon ion beam, to a diseased part (represented by a tumor) for treatment.

2. Description of the Related Art

There is known a therapy method for irradiating a charged particle beam (ion beam), e.g., a proton or carbon ion beam, to a tumor such as a cancer in the body of a patient. A charged particle beam extraction system (ion beam extraction system) for use in such therapy comprises a charged particle beam generator, a beam transportation line, and an irradiation apparatus. An ion beam accelerated by the charged particle beam generator reaches the irradiation apparatus through a first beam transportation line and a second beam transportation line, the irradiation apparatus and the second beam transportation line being installed in a rotating gantry. The ion beam is extracted from the irradiation apparatus and irradiated to the tumor in the patient body. Known examples of the charged particle beam generator include means for circulating the charged particle beam along an orbit, means for bringing betatron oscillation of the charged particle beam into a resonant state outside the separatrix of resonance, and a synchrotron (circular accelerator) provided with an extraction deflector for extracting the charged particle beam from the orbit (see, e.g., Patent Reference 1; U.S. Pat. No. 5,363,008).

The therapy using an ion beam, in particular, the treatment with irradiation of a proton beam to a tumor, is based on characteristics that most of energy of the proton beam is released at the time when protons are stopped, namely that a Bragg peak is formed upon the stop of protons. Then, the energy of the proton beam is selected to stop protons near the tumor so that most of the energy (absorbed dose) is given only to cells of the tumor.

Usually, a tumor has a certain thickness in the direction of depth from the body surface of a patient (hereinafter referred to simply as "the direction of depth", while it is coincident with the direction of travel of the ion beam). To effectively irradiate the ion beam over the entire thickness of the tumor in the direction of depth, the energy of the ion beam must be adjusted so as to form a comparatively wide and flat range of absorbed dose in the direction of depth (i.e., a spread-out Bragg peak width, hereinafter referred to as an "SOBP width").

From that point of view, a range modulation wheel (hereinafter abbreviated to "RMW") has already been proposed in which a plurality of blades each having a thickness varied step by step in the circumferential direction are disposed around a rotary shaft (see, e.g., Non-Patent Reference 1; "REVIEW OF SCIENTIFIC INSTRUMENTS", Vol. 64, No. 8, pp. 2074-2084 and FIGS. 30-32, in particular, p. 2077 and FIG. 30 (August 1993)). In the RMW, the plurality of blades are mounted to the rotary shaft, and a through opening is formed between adjacent two of the blades. By rotating the RMW in a state where, for example, the opening is positioned on a path of the ion beam (hereinafter referred to simply as a "beam path"), the opening and the blade alternately intersect the beam path. At the time when the ion beam passes the opening, the energy of the ion beam is not attenuated and therefore the Bragg peak is produced in the deepest position inside the patient body. At the time when the ion beam passes the blade, the energy of the ion beam is attenuated at a larger rate as the ion beam passes the blade having a larger thickness, and therefore the Bragg peak is produced in a portion closer to the body surface of the patient. With the rotation of the RMW, the position in the direction of depth where the Bragg peak is formed varies cyclically. As a result, the Bragg peak width being comparatively wide and flat in the direction of depth of the tumor can be obtained, looking at the beam energy integrated over time. Further, it is known that the SOBP width can also be formed by using a ridge filter (see, e.g., Non-Patent Reference 1; in particular, p. 2078 and FIG. 31).

SUMMARY OF THE INVENTION

One of three inventors of this application has previously invented and filed a charged particle beam extraction system for performing on/off-control of extraction of an ion beam from a synchrotron during the rotation of the RMW. With that preceding invention, by rotating the RMW such that the ion beam passes the RMW for a comparatively long time, i.e., over a wider range of RMW rotational angle, the attenuation of the ion beam is varied to a large extent, and hence the SOBP width is increased. On the other hand, by rotating the RMW such that the ion beam passes the RMW for a comparatively short time, i.e., over a narrower range of RMW rotational angle, the attenuation of the ion beam is varied to a small extent, and hence the SOBP width is decreased. Thus, the on/off-control of extraction of the ion beam during the rotation of the RMW enables the SOBP width to be produced in various values by using one RMW. It is therefore possible to reduce the frequency at which the RMW is to be replaced, and to smoothly carry out the treatment for a larger number of patients.

Further studies conducted by the inventors of this application on the preceding invention, however, showed that the preceding invention had yet room for improvement in the point given below.

According to the preceding invention, by performing the on/off-control of the beam extraction for each patient, the SOBP width can be obtained depending on the tumor in the body of the relevant patient. However, there has not yet been established a method for confirming in real time during the beam irradiation whether the beam is turned on and off at the desired timing. In other words, a further improvement is demanded from the viewpoint of ensuring higher safety in treatment.

It is an object of the present invention to provide a charged particle beam extraction system and method, which are able to ensure higher safety when extraction of an ion beam is on/off-controlled during irradiation of the ion beam for treatment.

To achieve the above object, the charged particle beam extraction system of the present invention is featured in comprising a wheel having a thickness varied in the direction of travel of a charged particle beam extracted from a charged particle beam generator such that energy of the charged particle beam passing the wheel is changed to form a spread-out Bragg peak width in an irradiation target, a first control unit for controlling start and stop of extraction of the charged particle beam from the charged particle beam generator in accordance with a rotational angle of the wheel, and a determination unit for determining whether the start and stop of extraction of the charged particle beam is controlled at desired timing by the first control unit.

With the present invention, since whether the start and stop of extraction of the charged particle beam is controlled at the desired timing during irradiation for treatment is determined, safety in the irradiation for treatment can be increased.

Preferably, the system is controlled so as to stop the extraction of the charged particle beam when it is determined that the start and stop of extraction of the charged particle beam is not controlled at the desired timing. This feature contributes to positively increasing safety in the treatment using the charged particle beam irradiated to the irradiation target.

Thus, according to the present invention, higher safety can be ensured in the treatment using the charged particle beam irradiated to the irradiation target.

BRIEF DESCRIPTION OF THE DRAWINGS

FIG. 9 is a table for explaining one example of treatment plan information stored in a memory of an irradiation controller shown in FIG. 2;

DESCRIPTION OF THE PREFERRED EMBODIMENTS

Embodiments of the present invention will be described in detail below with reference to the drawings.

First Emobodiment

Figure 1:
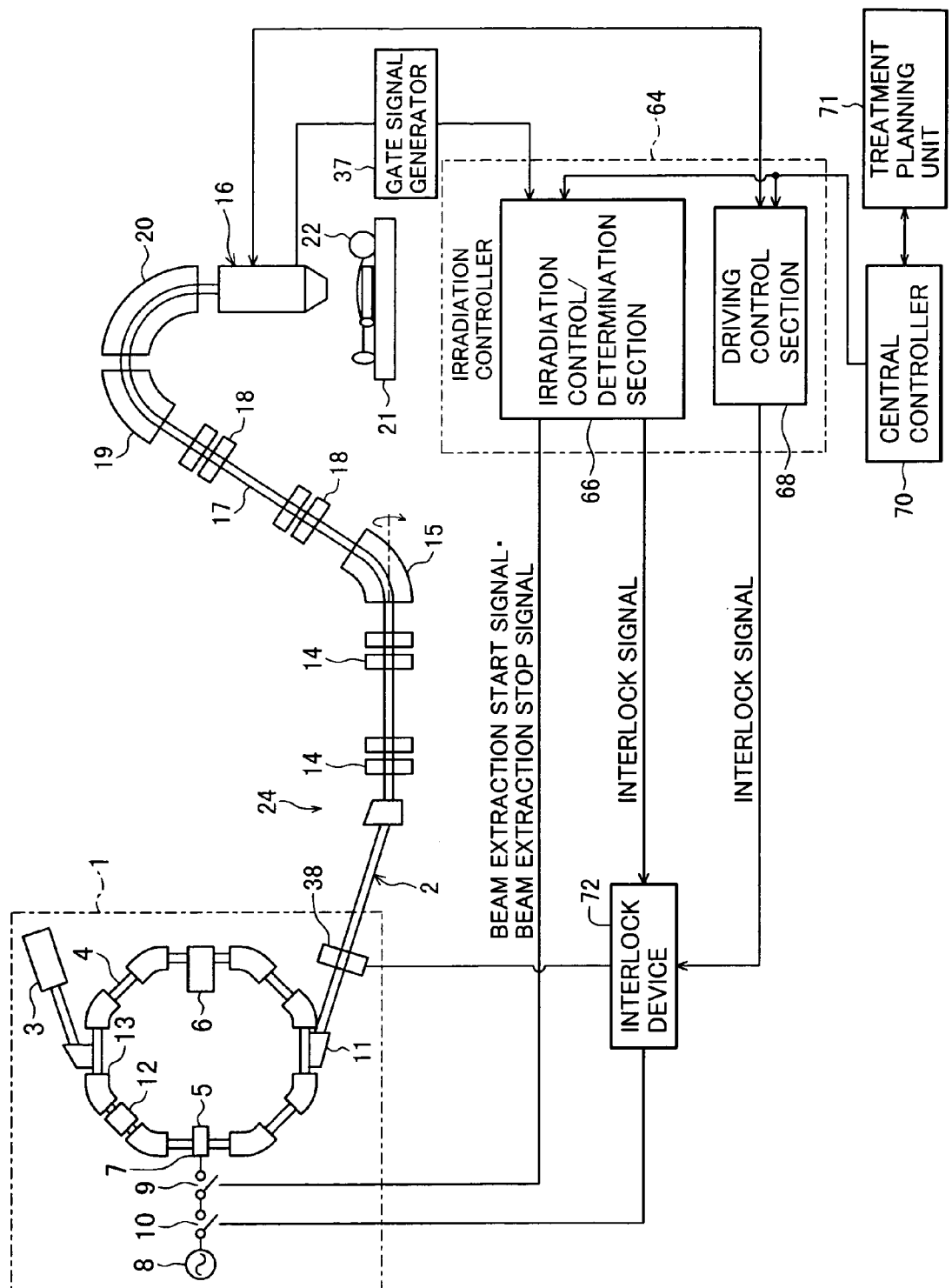
FIG. 1 is an overall block diagram of a charged particle beam extraction system according to a first embodiment of the present invention.

A charged particle beam extraction system as one preferred embodiment of the present invention will be described with reference to FIG. 1. The charged particle beam extraction system 24 of this embodiment comprises a charged particle beam generator 1, a beam transportation line 2 connected to the charged particle beam generator 1 at the downstream side thereof, and an irradiation apparatus 16 serving as an irradiation field forming apparatus. To be more specific, the charged particle beam extraction system 24 of this embodiment is a proton beam extraction system.

The charged particle beam generator 1 comprises an ion source (not shown), a pre-accelerator (e.g., a linear accelerator) 3, and a synchrotron 4 serving as a main accelerator. The synchrotron 4 includes an RF knockout electrode 5 made of paired electrode members and an RF cavity 6, which are disposed on an orbit of a circulating ion beam. A first RF power supply 8 is connected to the paired electrode members of the RF knockout electrode 5 through on/off switches 9, 10. A second RF power supply (not shown) for applying an RF power to the RF cavity 6 is separately provided. Ions (e.g., proton ions (or carbon ions)) generated from the ion source are accelerated by the pre-accelerator 3. An ion beam (charged particle beam) emitted from the pre-accelerator 3 enters the synchrotron 4. The ion beam, i.e., the charged particle beam, is given with energy and accelerated by an electromagnetic field generated in the RF cavity 6 with application of the RF power supplied from the second RF power supply. The ion beam circulating in the synchrotron 4 is extracted from the synchrotron 4 upon closing of the on/off switch 9 after the ion beam has been accelerated to have energy at a setting level (e.g., 100 to 200 MeV). More specifically, when the on/off switch 9 is closed, an RF wave supplied from the first RF-power supply 8 is applied to the circulating ion beam from the RF knockout electrode 5 through the on/off switch 10 held in the closed state and the closed on/off switch 9. With the application of the RF wave, the ion beam circulating within the separatrix is forced to transit out of the separatrix and to exit from the synchrotron 4 through a beam extraction deflector 11. At the time of extracting the ion beam, currents supplied to quadrupole magnets 12 and bending magnets 13 both disposed in the synchrotron 4 are held at setting current values, and hence the separatrix is also held substantially constant. The extraction of the ion beam from the synchrotron 4 is stopped by opening the on/off switch 9 (or the on/off switch 10) to stop the application of the RF power to the RF knockout electrode 5.

The ion beam extracted from the synchrotron 4 is transported to a beam passage 17 on the downstream side by the beam transportation line 2. The beam transportation line 2 includes quadrupole magnets 14 and bending magnets 15, and it is connected to the beam passage 17 communicating with the irradiation apparatus 16. The irradiation apparatus 16 and the beam passage 17 are both mounted to a rotating gantry (not shown) installed in a treatment room (not shown). Further, quadrupole magnets 18, a bending magnet 19, and a bending magnet 20 are disposed along the beam passage 17 in this order. The ion beam in the beam passage 17 is transported to the irradiation apparatus 16. A patient 22 lies on a treatment couch 21 properly positioned in a treatment cage (not shown) that is formed within the rotating gantry. The ion beam extracted from the irradiation apparatus 16 is irradiated to a tumor K (see FIG. 2 described later), such as a cancer, in the body of the patient 22. The beam passage 17 including the magnets, such as the quadrupole magnets 18, can also be regarded as a beam transportation line. In addition, a beam shutter 38 is disposed upstream of the beam transportation line 2. The beam shutter 38 is usually opened, but it is closed by a later-described interlock device 72 in the event of an abnormality, to thereby shut off the extraction of the ion beam from the synchrotron 4 (as described later in detail).

Figure 2:
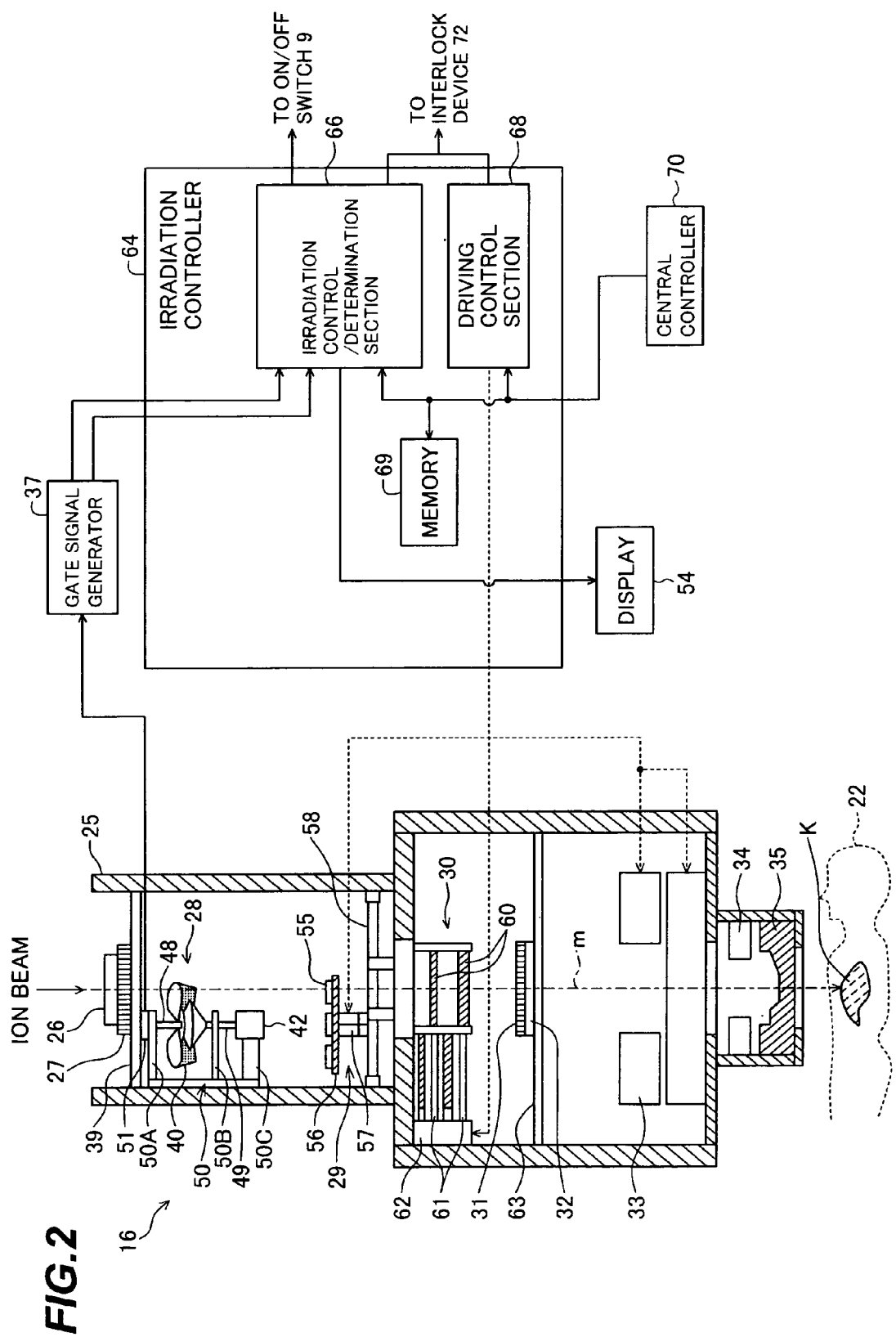
FIG. 2 is a vertical sectional view showing a detailed structure of an irradiation apparatus shown in FIG. 1.

The structure of the irradiation apparatus 16 will be described below with reference to FIG. 2. As shown in FIG. 2, the irradiation apparatus 16 has a casing 25 that is mounted to the rotating gantry and connected to the beam passage 17. Within the casing 25, the irradiation apparatus 16 has a beam profile monitor 26, a dose monitor 27, an RMW (range modulation wheel) device 28, a second scatterer device 29, a range adjustment device (e.g., a range shifter) 30, a dose monitor 31, a flatness monitor 32, a block collimator 33, a patient collimator 34, and a bolus 35, which are disposed to lie on a beam path (beam axis) m within the casing 25 in this order from the upstream side in the direction of travel of the ion beam.

The beam profile monitor 26 is a monitor for confirming whether the ion beam having entered the irradiation apparatus 16 from the beam transportation line 2 is positioned on the beam axis m. The dose monitor 27 is a monitor for detecting the dose of the ion beam having entered the irradiation apparatus 16. The beam profile monitor 26 and the dose monitor 27 are both installed on a support table 39 mounted to the casing 25.

Figure 3:
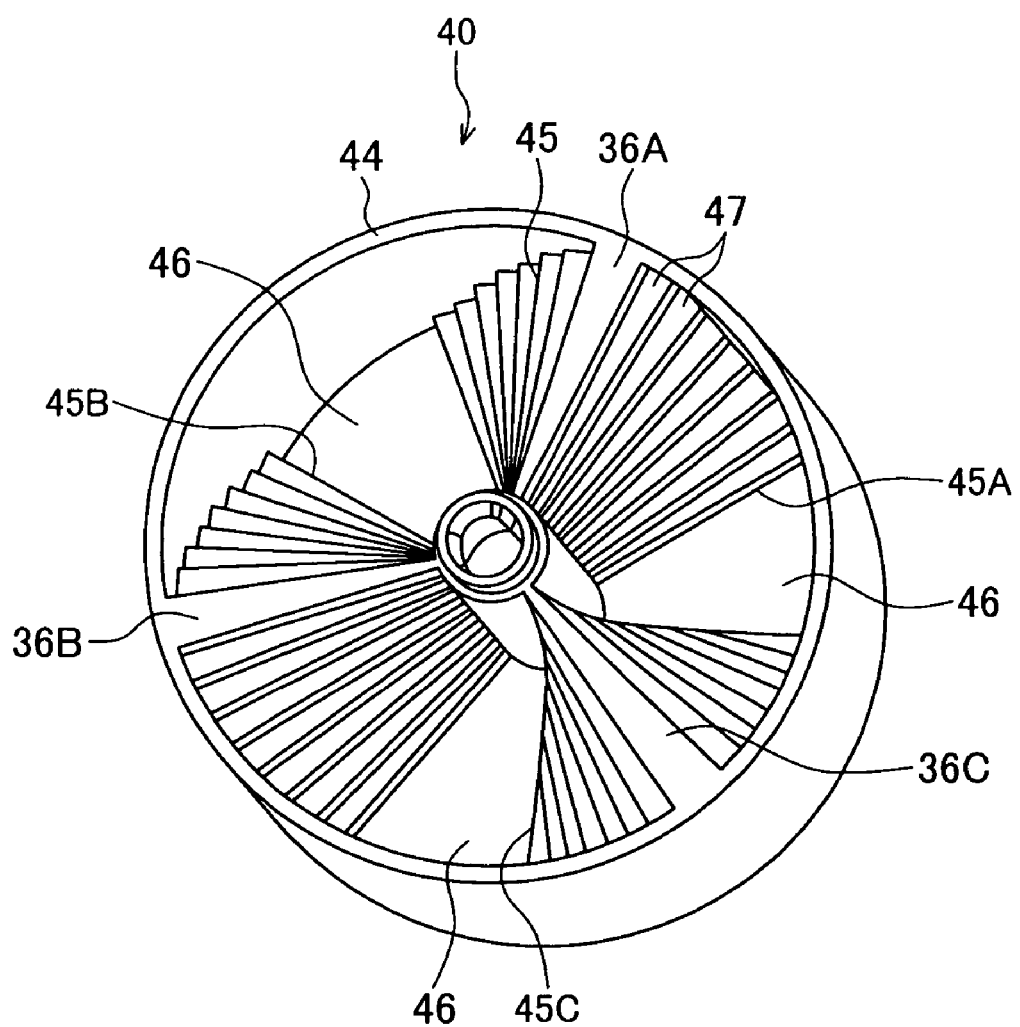
FIG. 3 is a perspective view of an RMW shown in FIG. 1.

The RMW device 28 comprises an RMW (wheel) 40, a rotation device (e.g., a motor) 42 for rotating the RMW 40, and an angle meter 51 for detecting the rotational angle of the RMW 40. The RMW 40, the rotation device 42, and the angle meter 51 are held by a support member 50 mounted to the casing 25. As shown in FIG. 3, the RMW 40 comprises a rotary shaft 43, a cylindrical member 44 disposed in a concentric relation to the rotary shaft 43, and a plurality of blades 45 (three blades 45A, 45B and 45C in this embodiment) each of which is mounted at one end to the rotatary shaft 43, is extended in the radial direction of the RMW 40, and is mounted at the other end to the cylindrical member 44. Each of the blades 45 has a circumferential width larger at the other end nearer to the cylindrical member 44 than at one end nearer to the rotary shaft 43. An opening 46 is formed between adjacent two of the blades 45 in the circumferential direction of the RMW 40. The opening 46 is also formed such that its circumferential width gradually increases toward an inner surface of the cylindrical member 44.

Each of the blades 45 has a plurality of plane areas (stepped portions) 47 arranged in the form of stairs in the circumferential direction of the RMW 40. Each of the plane areas 47 has a different thickness relative to a bottom surface of the RMW 40 in the axial direction of the rotary shaft 43 (i.e., the direction of the beam axis m). In other words, levels of the plane areas 47 relative to the bottom surface of the RMW 40 differ from one another. The thickness of each plane area 47 is called here the plane area thickness. More specifically, the plane area thickness of the blade 45 is increased in a stepwise way from each of the plane areas 47 adjacent to the openings 46, which are positioned on both sides of the relevant blade 45 in the circumferential direction, toward the plane area 47 positioned at a top portion 36 having the largest thickness in the direction of the beam axis m. Each plane area 47 is extended from the rotary shaft 43 toward the cylindrical member 44 and has a circumferential width gradually increasing toward the cylindrical member 44.

In an ideal form, the thickness of the RMW blade is changed continuously. However, an actual RWM is generally formed such that the blade thickness changes in a stepwise manner as described above. This is resulted from the viewpoint of tradeoff between an SOBP producing characteristic and workability in machining. Stated another way, the workability in machining (i.e., easiness in ensuring the machining accuracy) can be drastically improved in return for a slight reduction of the SOBP producing characteristic as compared with the case of the blade having the ideal form.

Returning to FIG. 2, the support member 50 mounted to the casing 25 has supports 50A, 50B opposing to each other in the direction of the beam axis m, and it also has a support 50C located downstream of the support 50B. The supports 50A, 50B rotatably support rotary shafts 48, 49, respectively. The RMW 40 is disposed between the supports 50A and 50B, and the rotary shaft 43 of the RMW 40 is supported by the rotary shafts 48, 49 in a sandwiched relation. More specifically, the rotary shaft 43 of the RMW 40 is detachably mounted to the rotary shafts 48, 49 so that the RMW 40 is replaceable. Respective opposed ends of the rotary shafts 48, 49 are inserted in through holes formed in the rotary shaft 43. The supports 50A, 50B are disposed in positions not interfering with the beam path within the casing 25. The rotary shafts 43, 48 and 49 are also disposed in positions away from the beam path.

The rotation device 42 mounted to the support 50C is coupled to the rotary shaft 49. The angle meter 51 for detecting the rotational angle (rotational phase) of the RMW 40 is coupled to the rotary shaft 48 and is mounted to the support 50A. A measured value of the rotational angle of the RMW 40 detected by the angle meter 51 is outputted to a gate signal generator 37 described later.

In this embodiment, though not shown in FIGS. 2 and 3, a first scatterer is further disposed on the beam axis m between the RMW device 28 and the second scatterer device 29. The first scatterer is also mounted to the casing 25. The first scatterer has the function of spreading the ion beam having passed the RMW 40 in the direction perpendicular to the beam axis m.

The second scatterer device 29 comprises a plurality of second scatterers 55, a rotating table 56, and a motor 57. The motor 57 is installed on a support member 58 that is mounted to the casing 25. The plurality of second scatterers 55 for scattering the ion beam at degrees different from one another are arranged on the rotating table 56 side by side in the circumferential direction thereof. With the rotating table 56 rotated by the motor 57, a predetermined one of the second scatterers 55 is positioned on the beam axis m. Driving of the motor 57 is controlled by a driving control section 68.

The range adjustment device 30 comprises a plurality (four in this embodiment) of absorbers 60 differing in thickness from one another, and an absorber operating device 61 provided for each of the absorbers 60. The absorber operating device 61 is constituted as, e.g., an air cylinder driven by compressed air. Each absorber operating device 61 is driven by an absorber driver 62 that is controlled by the driving control section 68.

The dose monitor 31 detects the dose of the ion beam having entered the irradiation apparatus 16 and having passed the RMW device 28, the first scatterer, the second scatterer device 29, and the range adjustment device 30. The flatness monitor 32 is a monitor for confirming flatness (dose uniformity) of the ion beam in the direction perpendicular to the beam axis m after being scattered by the first scatterer and the second scatterer device 55. The dose monitor 31 and the flatness monitor 32 are disposed on a support table 63.

The block collimator 33 shapes the ion beam in the planar direction perpendicular to the beam axis m, thereby roughly collimating the irradiation field of the ion beam. The aperture size of the block collimator 33 is variably controlled by the driving control section 68. The patient collimator 34 finely collimates the ion beam in match with the shape of the tumor K in the body of the patient 22. The bolus 35 has the function of adjusting a penetration depth of the ion beam in match with the maximum depth of the tumor K (which represents the diseased part suffering from a cancer or a tumor) in the body of the patient 22 under treatment. Stated another way, the bolus 35 adjusts the range of the ion beam at each position on a plane perpendicular to the beam axis m in match with the shape of the tumor K as an irradiation target in the direction of depth thereof.

The charged particle beam extraction system 24 includes a gate signal generator (first control unit) 37 and an irradiation controller 64. The irradiation controller 64 comprises an irradiation control/determination section (determination unit and third control unit) 66, the driving control section 68, and a memory 69.

The gate signal generator 37 generates and outputs a gate signal (first control signal) depending on the rotational angle of the RMW 40, which is inputted from the angle sensor 51. More specifically, the gate signal generator 37 receives and counts output pulses outputted from an encoder (not shown). The encoder is incorporated in the angle sensor 51 and is rotated in sync with the RMW 40. Then, the output of the gate signal is turned on or off when the count value of the output pulses matches with a count target value of the encoder output pulses which corresponds to the timing of turning on or off the output of the gate signal and is stored in a memory (not shown) in the gate signal generator 37 beforehand. Also, the gate signal generator 37 outputs a reference signal (pulse signal) per rotation of the RMW 40, which serves as a reference for the output timing of the gate signal. More specifically, as in the above case outputting the gate signal, a count target value of the encoder output pulses corresponding to the timing of outputting the reference signal is stored in the gate signal generator 37 beforehand, and the reference signal is outputted when the count value of the output pulses matches with that count target value. While the gate signal generator 37 is shown in FIG. 2 as being separately disposed from the irradiation controller 64, it may be alternatively incorporated in the irradiation controller 64 as one function thereof.

The irradiation control/determination section 66 receives the gate signal outputted form the gate signal generator 37 and determines whether turning-on or -off of the output of the gate signal is made at the desired timing. If it is determined that the output timing is normal, the irradiation control/determination section 66 executes on/off-control of extraction of the ion beam from the charged particle beam generator 1 to form the SOBP width in accordance with the gate signal. If it is determined that the output timing is abnormal, the section 66 makes control to stop the extraction of the ion beam from the charged particle beam generator 1 and to close the beam shutter 38 via the interlock device 72. The driving control section 68 controls respective operations for driving the motor 57 of the second scatterer device 29, the absorber driver 62 of the range adjusting device 30, and the block collimator 33. The memory 69 stores various target values (described in more detail later) used for determining the on/off-timing of the output of the gate signal, and irradiation condition information outputted from a central controller 70. The charged particle beam extraction system 24 further includes the interlock device 72 (see FIG. 1).

In the charged particle beam extraction system 24 thus constructed, a plurality of SOBP widths can be formed by performing the on/off-control of extraction of the ion beam from the charged particle beam generator 1 depending on the rotational angle of the RMW 40. The principle of that on/off-control of the ion beam extraction will be described below with reference to FIGS. 4, 5 and 6.

At the time when the ion beam passes the opening 46 of the RMW 40, the beam energy is not attenuated and therefore the Bragg peak is formed in a first deep position away from the body surface. At the time when the ion beam passes the plane area 47 of the blade 45 which is positioned at the top portion 36 and has the largest thickness, the beam energy is maximally attenuated and therefore the Bragg peak is formed in a second shallow position close to the body surface. At the time when the ion beam passes the plane area 47 positioned between the opening 46 and the top portion 36, the beam energy is attenuated at a rate depending on the blade thickness at the position where the relevant plane area 47 is present, and therefore the Bragg peak is formed in a third position between the first position and the second position. Accordingly, when the ion beam is always turned on all over a 360°-region of the rotational angle in the circumferential direction of the RMW 40 as the case a shown in FIGS. 4 and 5, the Bragg peak cyclically varies between the first position and the second position with the rotation of the RMW 40. As a result, looking at the dose integrated over time, the case a can provide a comparatively wide SOBP width ranging from a position near the body surface to a deep position as indicated by a dose distribution a in the direction of depth, as shown in FIG. 6. The term "beam-on" means a state in which the ion beam is extracted from the synchrotron 4 and irradiated from the irradiation apparatus 16 after passing the RMW 40. On the other hand, the term "beam-off" means a state in which the ion beam is not extracted from the synchrotron 4 and hence not irradiated from the irradiation apparatus 16.

Figure 4:
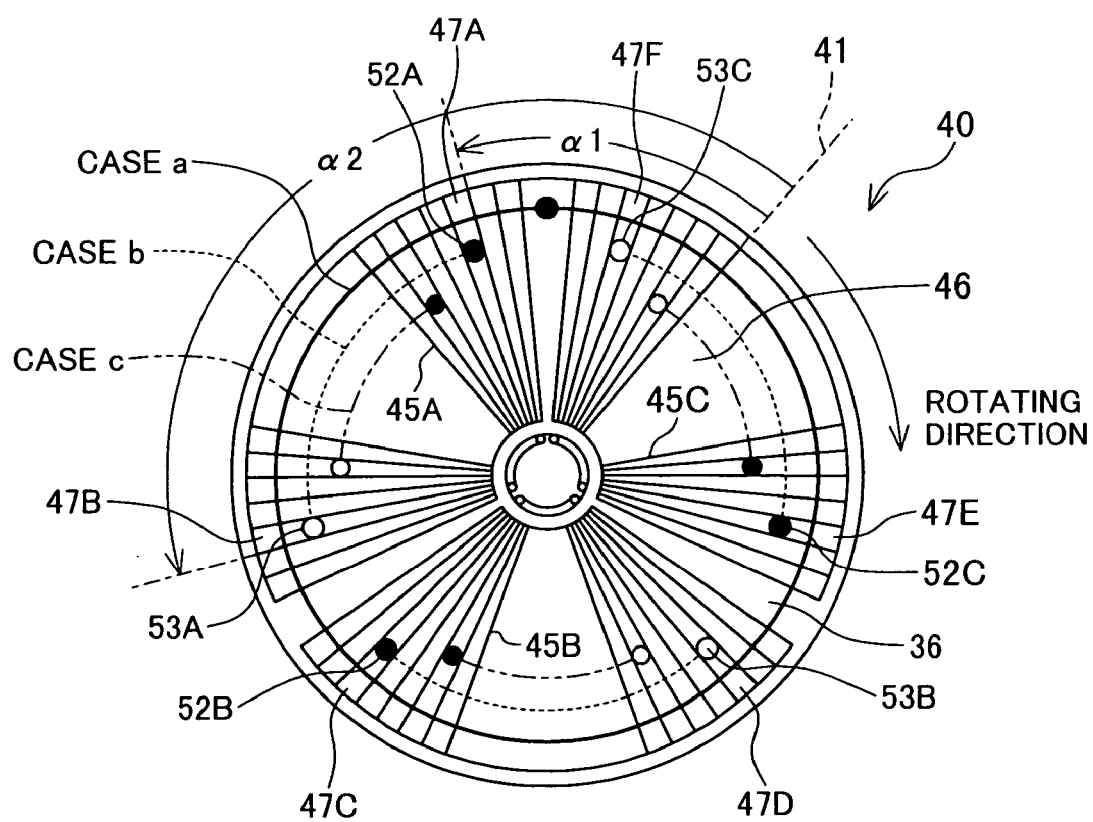
FIG. 4 is a plan view of the RMW shown in FIG. 3, the view showing, by way of example, ion beam extraction cases a to c.
Figure 5:
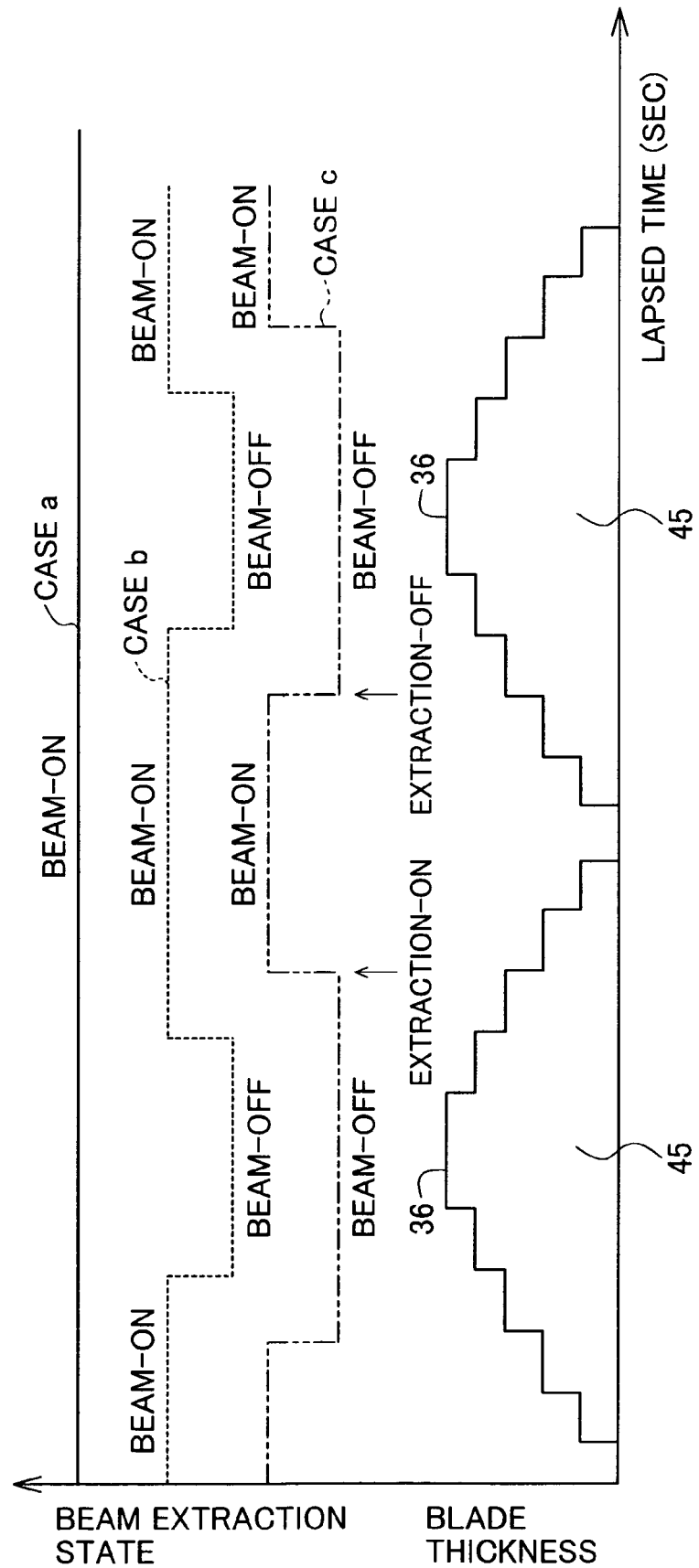
FIG. 5 is a chart showing beam-on and beam-off periods in each of the cases a to c, shown in FIG. 4, on the time serial basis.
Figure 6:
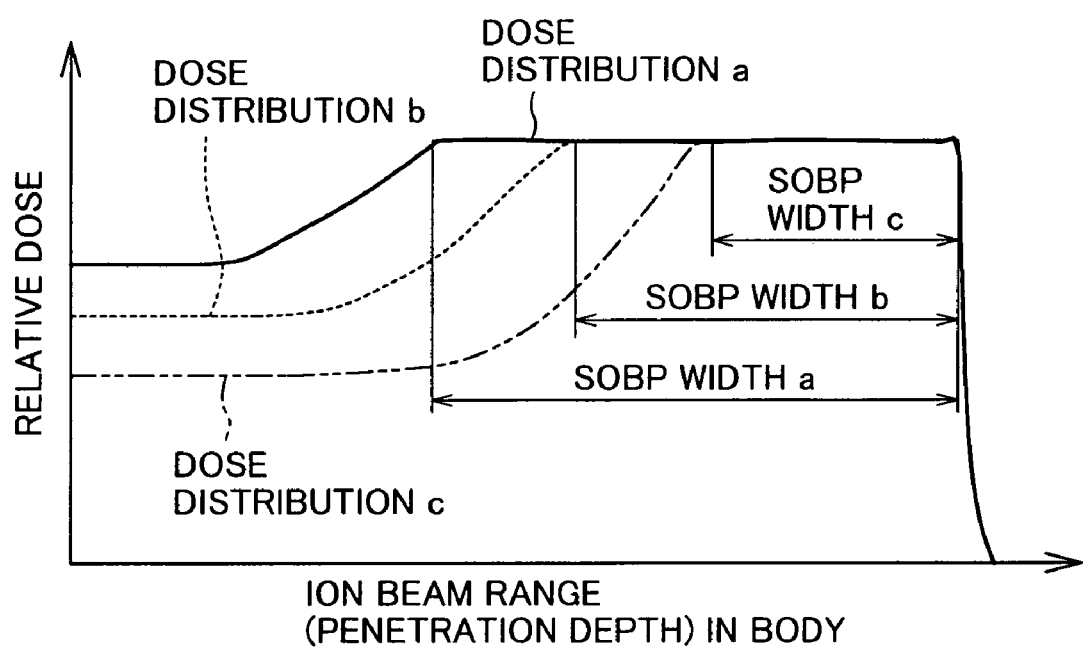
FIG. 6 is a graph showing a dose distribution and an SOBP width in the direction of depth in each of the cases a to c shown in FIG. 4.

In the case b shown in FIGS. 4 and 5, the ion beam is turned off in a comparatively thick region (near the top portion 36) of each blade 45 in the circumferential direction of the RMW 40, while the ion beam is turned on in the other region of the rotational angle. Because no Bragg peak is formed in a shallow portion near the body surface, the case b provides an SOBP width indicated by a dose distribution b in the direction of depth and having a narrower flat zone than the dose distribution a, as shown in FIG. 6.

In the case c shown in FIGS. 4 and 5, the ion beam is turned on in the opening 46 and a comparatively thin region of each blade 45 near the opening 46 in the circumferential direction of the RMW 40, while the ion beam is turned off in the other region of the rotational angle. Because the attenuation rate of the beam energy is small as a whole, the Bragg peak is formed in a deep position away from the body surface in the case c. Therefore, the case c provides an SOBP width indicated by a dose distribution c in the direction of depth and having a narrower flat zone than the dose distribution b, as shown in FIG. 6.

Thus, the charged particle beam extraction system 24 can form a plurality of different SOBP widths with one unit of RMW by performing the on/off-control of extraction of the ion beam depending on the rotational angle of the RMW 40 as described above.

The capability of forming various SOBP widths by the on/off-control of extraction of the ion beam performed during the rotation of the RMW 40 is much merit as described later. On the other hand, a capability of confirming whether the on/off-control of extraction of the ion beam is actually performed at the desired timing or not is one of important factors required for the charged particle beam extraction system from the viewpoint of increasing safety in the treatment using the ion beam. The inventors of this application have conducted various studies with intent to overcome such a problem. Results of the studies conducted by the inventors will be described below.

Figure 7:
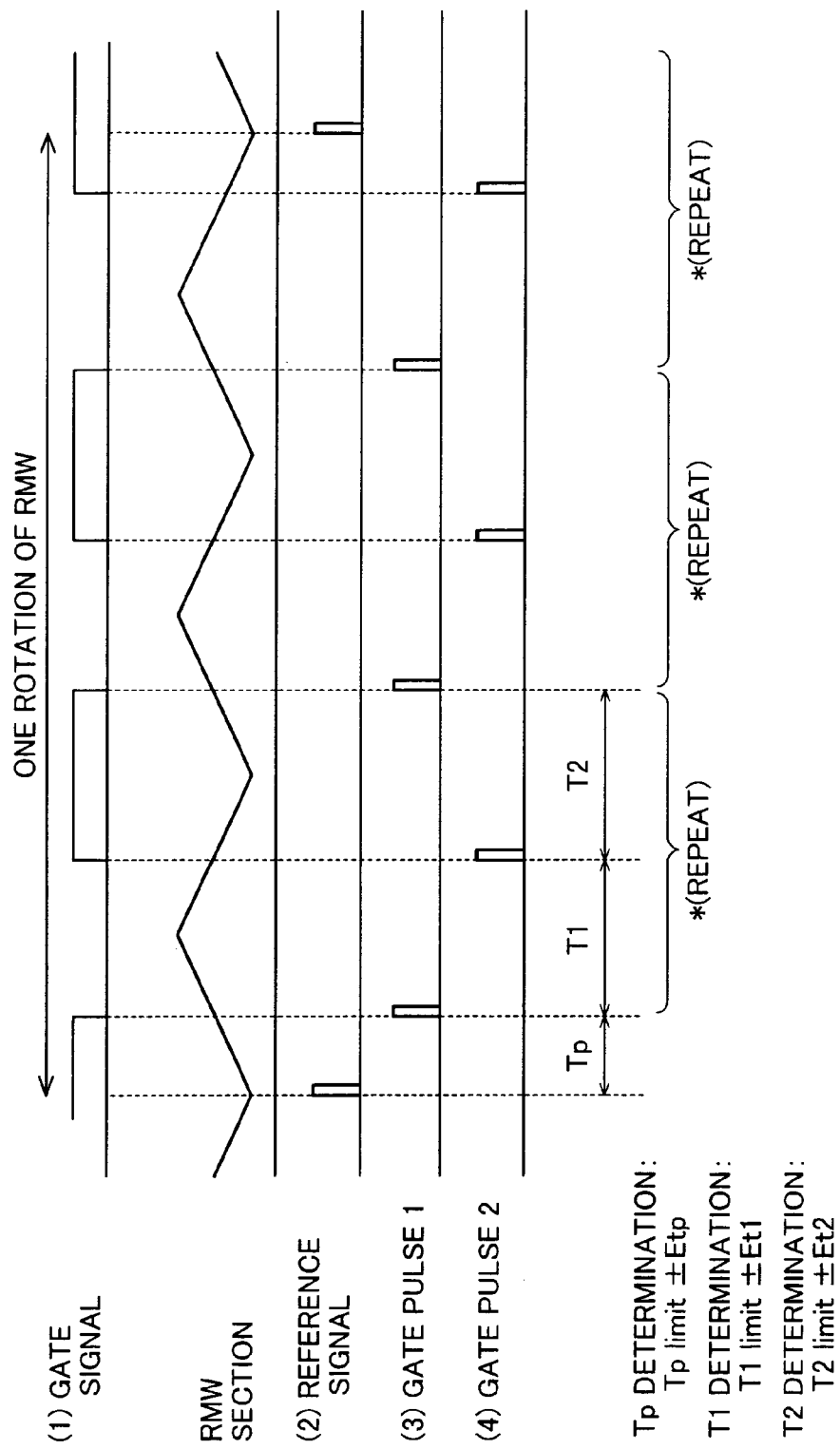
FIG. 7 is a time chart showing the relationship between rotation of the RMW shown in FIG. 3 and a gate signal.

FIG. 7 is a time chart showing the relationship between the rotation of the RMW 40 and the gate signal. While the thickness of the RMW blade is changed in a stepwise manner in the above description with reference to FIGS. 3 through 5, such a blade shape is resulted, as mentioned above, from the restriction in ensuring high machining accuracy with ease. In the following description with reference to FIG. 7 and subsequent drawings, it is assumed that the RMW blade has a mountain-like sectional shape with the thickness changing ideally linearly. From the viewpoint of description, there is no essential difference between the case of the blade having a mountain-like sectional shape and the case of the blade having the thickness changed in a stepwise manner. As described above with reference to FIG. 3, the RMW 40 has the three blades 45A, 45B and 45C, and therefore has a section projecting in three mountain-like shapes in the circumferential direction as shown in FIG. 7. In the illustrated example, there are three mountains (blade portions each having the maximum thickness) and three valleys (portions having zero thickness (i.e., portions corresponding to the openings 46 in FIG. 4)). The gate signal is controlled such that it is turned on within a certain range about the bottom of each valley as in the case b described above with reference to FIG. 4. When the gate signal inputted from the gate signal generator 37 is turned on, the irradiation control/determination section 66 outputs an extraction start signal to the on/off switch 9 if there is no abnormality in later-described determinations. The extraction start signal closes the on/off switch 9 so that the RF wave supplied from the first RF-power supply 8 is applied to the circulating ion beam from the RF knockout electrode 5. When the gate signal inputted from the gate signal generator 37 is turned off, the irradiation control/determination section 66 outputs an extraction stop signal to the on/off switch 9, whereby the on/off switch 9 is opened to stop the application of the RF wave supplied from the first RF-power supply 8 to the ion beam from the RF knockout electrode 5.

Figure 8:
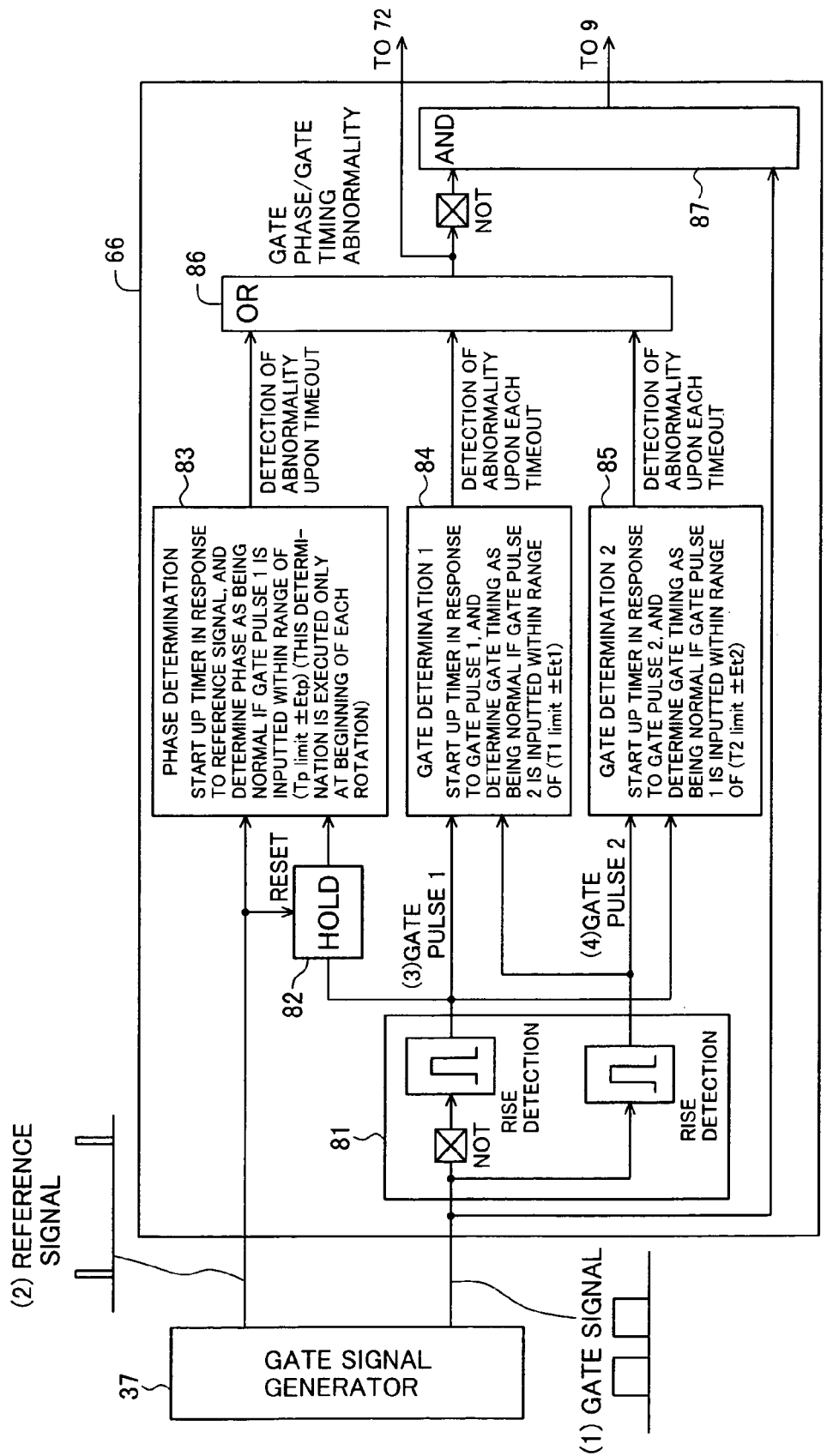
FIG. 8 is a functional block diagram showing the determining function of an irradiation control/determination section shown in FIG. 1.

With reference to FIG. 8, a description is now made of the function of determining the on/off-timing of the gate signal (hereinafter referred to simply as the "gate timing"), which is executed in the irradiation control/determination section 66. FIG. 8 is a functional block diagram showing the determining function of the irradiation control/determination section 66. As shown in FIG. 8, the gate signal (denoted by (1) in FIG. 8) and the reference signal (denoted by (2) in FIG. 8) are inputted to the irradiation control/determination section 66 from the gate signal generator 37. The reference signal inputted from the gate signal generator 37 is applied to a phase determination circuit 83, whereupon the phase determination circuit 83 starts up a not-shown timer (timer unit). On the other hand, the inputted gate signal is applied to an input processing circuit 81 where a rise or a fall of the gate signal is detected. When a fall of the gate signal is detected (in the illustrated example, when a rise of the gate signal is detected via a NOT circuit), a gate pulse-1 signal (denoted by (3) in FIG. 8) is inputted from the input processing circuit 81, via a hold circuit 82, to the phase determination circuit 83 for determination of a time Tp. The time Tp means a period of time from the reference signal to the first fall of the gate signal (see FIG. 7). More specifically, the phase determination circuit 83 compares the time Tp from the reference signal to the first fall of the gate signal with a target value, thereby determining a phase difference between the whole of the gate signal and the rotation of the RMW 40. In practice, the time Tp is determined as being normal if the following condition (i) is satisfied:

Tp determination:

$$Tp\ \text{limit} - Etp \leq Tp \leq Tp\ \text{limit} + Etp \qquad (i)$$

In the condition (i), "Tp limit" is the target value of Tp, and Etp is an allowable value of Tp, e.g., a value stored in the memory 69 of the irradiation controller 64 beforehand. Because the hold circuit 82 holds the gate pulse 1 until the reference signal is reset, the Tp determination is executed on the gate pulse 1 only once immediately after the reference signal per rotation of the RMW 40.

The gate pulse-1 signal (denoted by (3) in FIG. 8) from the input processing circuit 81 is further inputted to a gate determination-1 circuit 84. Then, when a rise of the gate signal is detected, a gate pulse-2 signal (denoted by (4) in FIG. 8) from the input processing circuit 81 is inputted to the gate determination 1 circuit 84 for determination of a time T1. The time T1 means a period of time from the gate pulse-1 signal to a gate pulse-2 signal (i.e., a time during which the gate signal is turned off) (see FIG. 7). More specifically, the gate determination-1 circuit 84 compares the time T1 from the gate pulse-1 signal to the gate pulse-2 signal with a target value, thereby determining the time T1 during which the gate signal is turned off. In practice, the time T1 is determined as being normal if the following condition (ii) is satisfied:

T1 determination:

$$T1\ \text{limit} - Et1 \leq T1 \leq T1\ \text{limit} + Et1 \qquad (ii)$$

In the condition (ii), "T1 limit" is the target value of T1, and Et1 is an allowable value of T1, e.g., a value stored in the memory 69 of the irradiation controller 64 beforehand. Because the blades 45 of the RMW 40 have a rotationally symmetric structure, the determination is repeatedly executed per blade 45 during one rotation of the RMW 40.

The gate pulse-2 signal (denoted by (4) in FIG. 8) from the input processing circuit 81 is further inputted to a gate determination-2 circuit 85. Then, when a fall of the gate signal is detected, the gate pulse-1 signal (denoted by (3) in FIG. 8) from the input processing circuit 81 is inputted to the gate determination-2 circuit 85 for determination of a time T2. The time T2 means a period of time from the gate pulse-2 signal to the gate pulse-1 signal (i.e., a time during which the gate signal is turned on) (see FIG. 7). More specifically, the gate determination-2 circuit 85 compares the time T2 from the gate pulse-2 signal to the gate pulse-1 signal with a target value, thereby determining the time T2 during which the gate signal is turned on. In practice, the time T2 is determined as being normal if the following condition (iii) is satisfied:

T2 determination:

$$T2\ \text{limit} - Et2 \leq T2 \leq T2\ \text{limit} + Et2 \qquad (iii)$$

In the condition (iii), "T2 limit" is the target value of T2, and Et2 is an allowable value of T2, e.g., a value stored in the memory 69 of the irradiation controller 64 beforehand. Because the blades 45 of the RMW 40 have a rotationally symmetric structure, the determination is repeatedly executed per blade 45 during one rotation of the RMW 40.

If the determination is not satisfied in any of the determination circuits 83, 84 and 85, a signal indicating detection of an abnormality is inputted to an OR circuit 86 which produces a gate phase/gate timing abnormality signal. This abnormality signal is applied to a succeeding AND circuit 87 via a NOT circuit. With such an arrangement, the AND circuit 87 provides the gate signal from the gate signal generator 37, as the beam extraction start signal or the beam extraction stop signal, to the on/off switch 9 only when the gate timing is normal, whereby the on/off-control of the beam extraction can be performed. Thus, if an abnormality of the gate timing is detected in any of the determination circuits 83, 84 and 85, the gate signal is not outputted to the on/off switch 9 (namely, the beam extraction stop signal is outputted). As a result, the on/off switch 9 is opened and the beam extraction from the synchrotron 4 is stopped. At the same time, an interlock signal is outputted to the interlock device 72, whereupon the interlock device 72 closes the beam shutter 38 to prevent the ion beam from being transported toward the irradiation apparatus 16.

Prior to starting the treatment using the charged particle beam extraction system 24, a doctor makes a diagnosis based on a tomogram of the tumor K and thereabout in the body of the patient 22, which is taken by using an X-ray CT apparatus (not shown). The doctor confirms the position and size of the tumor K with the diagnosis, and inputs information indicating the direction of irradiation of the ion beam, the maximum irradiation depth, etc. to a treatment planning unit 71. Based on the input information such as the direction of irradiation of the ion beam and the maximum irradiation depth, the treatment planning unit 71 computes the SOBP width, the irradiation field size, the target dose to be irradiated to the tumor K, etc. by using treatment planning software. Further, the treatment planning unit 71 computes various operation parameters (such as the energy of the ion beam at the time when it is extracted from the synchrotron 4 (i.e., the incident energy to the irradiation apparatus 16), the angle of the rotating gantry, and the rotational angles of the RMW 40 when the extraction of the ion beam is turned on and off), and then selects the RMW 40 suitable for the treatment. Those various items of treatment plan information including not only the rotational angles and the target dose, but also other items listed in FIG. 9, i.e., the irradiation field size, the range, the incident energy (incident Eg), the thickness of the first scatterer (SC1 thickness), the SOBP width, the type of the second scatterer 55 (SC2 type), the thickness of the absorber 60 positioned in the beam path within the range adjustment device 30 (RS thickness), and the aperture size of the block collimator 33 (BC aperture size), are inputted to the central controller 70 of the charged particle beam extraction system 24 and stored in a memory (not shown) of the central controller 70. The above-stated treatment plan information is stored in the memory 69 of the irradiation controller 64 as well from the central controller 70.

In accordance with the rotating gantry angle information inputted from the memory 69, a gantry controller (not shown) rotates the rotating gantry to direct the beam path within the irradiation apparatus 16 toward the patient 22. Then, the treatment couch 21 on which the patient is lying is moved and positioned such that the tumor K lies on an extension of the beam path within the irradiation apparatus 16.

By using the information stored in the memory 69 and regarding the irradiation field size, the range and the incident energy, the driving control section 68 of the irradiation controller 64 selects respective values of the thickness of the first scatterer, the SOBP width, the type of the second scatterer, the absorber thickness, and the aperture size of the block collimator from the irradiation condition information stored in the memory 69 beforehand, which is shown, by way of example, in FIG. 9. In accordance with the information regarding the thickness of the first scatterer, the driving control section 68 moves the first scatterer having the selected thickness to be positioned on the beam axis m. Then, the driving control section 68 drives the motor 57 to rotate the rotating table 56 such that the selected second scatterer 55 is positioned on the beam axis m. Further, the driving control section 68 actuates the absorber operating device 61 through the absorber driver 62 such that the selected absorber 60 is positioned on the beam axis m. In accordance with the information regarding the selected aperture size of the block collimator 33, the driving control section 68 controls a not-shown driver to move blocks of the block collimator 33 for setting the aperture size to a predetermined value.

The various items of the treatment plan information are displayed on a display installed in a control room for the charged particle beam extraction system 24. The RMW 40, the bolus 35, and the patient collimator 34, which are suitable for the patient 22 who is going to take the treatment, are installed in the casing 25 of the irradiation apparatus 16, as shown in FIG. 2, by an operator.

The irradiation control/determination section 66 of the irradiation controller 64 reads, from the memory 69, rotational angle information (e.g., $\alpha 1$ to $\alpha 6$ described later) of the RMW 40 installed in the casing 25, the target dose, the target values "Tp limit", "T1 limit" and "T2 limit" and the allowable values Etp, Et1 and Et2 used in the above-described Tp, T1 and T2 determinations, which are suitable for the patient 22 who is going to take the treatment.

A manner of treating the tumor K by using the charged particle beam extraction system 24 will be described below. The synchrotron 4 is operated by repeating the steps of introducing the ion beam from the pre-accelerator 3, and then accelerating, extracting and decelerating the ion beam. When the ion beam is accelerated until reaching the extraction energy at a setting level, the acceleration of the ion beam is brought to an end and the ion beam comes into a state ready for extraction from the synchrotron 4 (i.e., an ion beam extractable state). Information indicating the end of acceleration of the ion beam is transmitted to the central controller 70 from a magnet power supply controller that monitors states of the magnets, etc. of the synchrotron 4 by using sensors (not shown).

The on/off-control of extraction of the ion beam for forming the SOBP width, as described above, in the charged particle beam extraction system 24 will be described below with reference to FIGS. 1, 2, 4 and 10. The following description of the on/off-control of extraction of the ion beam is made, by way of example, in connection with the case b shown in FIG. 5. In the example of the case b, black points 52A, 52B and 52C each represent the timing of the extraction-on (start of extraction) of the ion beam, and white points 53A, 53B and 53C each represent the timing of the extraction-off (stop of extraction) of the ion beam. When the irradiation control/determination section 66 executes the control for the case b, it receives, from the memory 69, the rotational angles $\alpha 1$ to $\alpha 6$ ($\alpha 3$ to $\alpha 6$ being not shown), i.e., the setting values of the rotational angles. The rotational angle $\alpha 1$ represents an angle from a reference line 41 to the point 52A, and the rotational angle $\alpha 2$ represents an angle from the reference line 41 to the point 53A. The rotational angle $\alpha 3$ represents an angle from the reference line 41 to the point 52B, and the rotational angle α4 represents an angle from the reference line 41 to the point 53B. The rotational angle α5 represents an angle from the reference line 41 to the point 52C, and the rotational angle α6 represents an angle from the reference line 41 to the point 53C. The rotational angles α1 to α6 each represent an angle on the basis of the state in which the reference line 41 is positioned on the beam axis m. In FIG. 4, the position of each black point represents a position where the extraction of the ion beam is started, while the position of each white point represents a position where the extraction of the ion beam is stopped.

Figure 10:
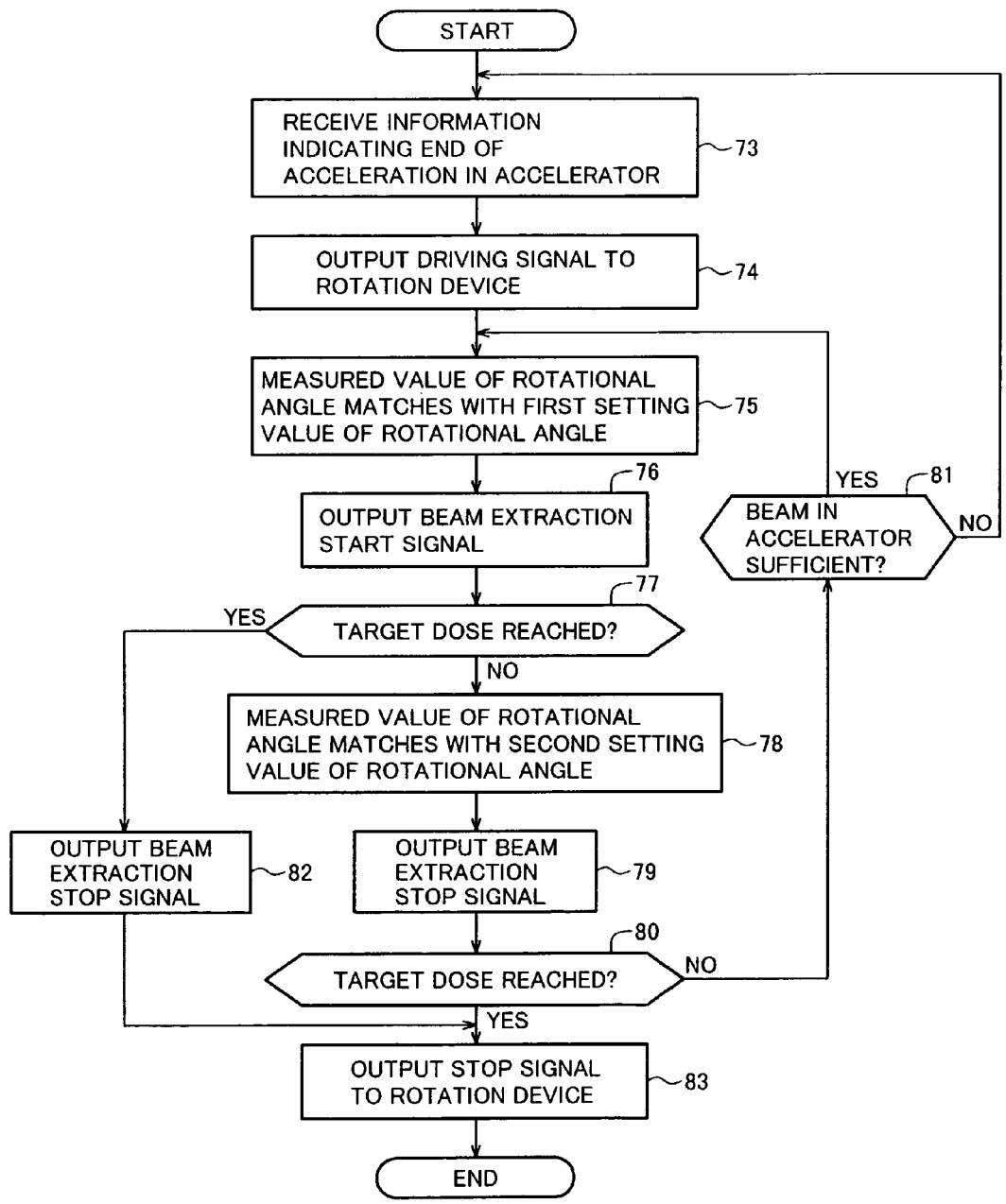
FIG. 10 is a flowchart showing control steps executed by the irradiation control/determination section shown in FIG. 1.

The irradiation control/determination section 66 executes the on/off-control of extraction of the ion beam in accordance with a control flow shown in FIG. 10. First, the irradiation control/determination section 66 receives a signal indicating the end of acceleration in the accelerator (synchrotron 4) (i.e., a signal indicating that the ion beam is in the extractable state) (step 73). The end-of-acceleration signal is inputted from the central controller 70. Then, the section 66 outputs a start-of-rotation signal to the rotation device 42 (step 74). The rotation device 42 is rotated in accordance with the start-of-rotation signal. The torque of the rotation device 42 is transmitted to the rotary shaft 43 through the rotary shaft 49, whereby the RMW 40 is rotated. The number of rotations of the RMW 40 is set to a value in the range of 100 to 200 rotations per second. It is determined whether a measured value of the rotational angle matches with a first setting value of the rotational angle (step 75). More specifically, a value of the rotational angle of the RMW 40 measured by the angle sensor 51 is inputted to the gate signal generator 37. It is then determined whether the input measured value matches with the first setting value of the rotational angle (any of the rotational angles α1, α3 and α5) at which the beam extraction start signal is to be outputted. If the measured value of the rotational angle matches with the first setting value, the gate signal is outputted from the gate signal generator 37 to the irradiation control/determination section 66. Then, if the gate timing is determined as being normal based on the Tp, T1 and T2 determinations, the beam extraction start signal is outputted from the irradiation control/determination section 66 (step 76). The on/off switch 9 is closed in response to the beam extraction start signal. The on/off switch 10 is held in the closed state. The RF wave outputted from the first RF-power supply 8 is applied to the circulating ion beam from the RF knockout electrode 5, whereupon the ion beam is extracted from the synchrotron 4. The extracted ion beam is transported to the irradiation apparatus 16.

The transported ion beam travels along the beam axis m within the irradiation apparatus 16. The ion beam passes the beam profile monitor 26 and the dose monitor 27. The ion beam having passed the rotating RMW 40 is spread out by the first scatterer in the direction perpendicular to the beam axis m. Then, the dose distribution of the ion beam is flattened by the second scatterer 55 in the direction perpendicular to the beam axis m. By subsequently passing the absorber 60 of the range adjusting device 30, the energy of the ion beam is reduced for adjustment of the range to be obtained in the body of the patient 22. The dose of the ion beam having passed the absorber 60 is measured by the dose monitor 31, and the flatness of the ion beam in the direction perpendicular to the beam axis m is confirmed by the flatness monitor 32. The ion beam further passes the block collimator 33, the patient collimator 34, and the bolus 35, followed by being irradiated to the tumor K.

It is determined whether the dose having been irradiated to the tumor K has reached the target dose (step 77). Further, it is determined whether the measured value of the rotational angle matches with a second setting value of the rotational angle (step 78). The dose having been irradiated to the tumor K is measured by the dose monitor 31 and is inputted to the irradiation control/determination section 66. In step 77, it is determined whether a total of the dose value measured by the dose monitor 31 has reached the target dose. If this determination result is "YES", the processing of step 82 is executed in precedence to the processing of step 78 and the beam extraction stop signal is outputted from the irradiation control/determination section 66 to the on/off switch 9. In response to the output of the beam extraction stop signal, the on/off switch 9 is opened to stop the supply of the RF power to the RF knockout electrode 5. Accordingly, the extraction of the ion beam from the synchrotron 4 is stopped and the irradiation of the ion beam toward the patient 22 lying on the treatment couch 21 is brought to an end. A stop-of-rotation signal is then outputted to the rotation device 42 (step 83). Responsively, the rotation device 42 stops its rotation and the rotation of the RMW 40 is also stopped.

If the determination result in step 77 is "NO", the processing of step 78 is executed. If it is determined in step 78 that the measured value of the rotational angle inputted to the gate signal generator 37 matches with the second setting value of the rotational angle (any of the rotational angles α2, α4 and α6) at which the beam extraction stop signal is to be outputted, the gate signal outputted from the gate signal generator 37 to the irradiation control/determination section 66 is turned off, whereby the beam extraction stop signal is outputted from the irradiation control/determination section 66 (step 79). In response to the output of the beam extraction stop signal, as mentioned above, the on/off switch 9 is opened and the extraction of the ion beam from the synchrotron 4 is stopped. The period from the output of the beam extraction start signal in step 76 to the output of the beam extraction stop signal in step 79 represents a period during which, for example, a region from the plane area 47A of the blade 45A to the plane area 47B of the blade 45B intersects the beam axis m along which the ion beam travels, i.e., an effective beam-on period. The time taken from the closing of the on/off switch 9 to the start of extraction of the ion beam from the synchrotron 4 is not longer than $\frac{1}{1000}$ sec, and conversely the time taken from the opening of the on/off switch 9 to the stop of extraction of the ion beam is also not longer than $\frac{1}{1000}$ sec.

In step 80, it is determined again whether the dose having been irradiated to the tumor K, which is determined based on the measured signal from the true dose monitor 31, has reached the target dose. If this determination result is "NO", the processing of step 81 is executed. Stated another way, it is determined whether a sufficient amount of the ion beam exists in the synchrotron 4 after the end of the beam-on period. The amount of the ion beam (i.e., the current density of the ion beam) present in the synchrotron 4 is monitored by the magnet power supply controller based on a value measured by a sensor (not shown) disposed in the synchrotron 4. The measured value of the current density of the ion beam is inputted to the irradiation control/-determination section 66 via the central controller 70. The determination in step 81 is made using the measured value of the current density. If the determination result in step 81 is "YES", the processing of steps 75 to 80 is executed again. The period from the output of the beam extraction start signal in step 76 to the output of the beam extraction stop signal in step 79 in this repeated processing represents a period during which, for example, a region from the plane area 47C of the blade 45B to the plane area 47D of the blade 45C intersects the beam axis m, i.e., an effective beam-on period. The period during which, for example, a region from the plane area 47E of the blade 45C to the plane area 47F of the blade 45A intersects the beam axis m in the next repeated processing of steps 75 to 80 also represents an effective beam-on period. Between the two beam-on periods adjacent to each other, there is a beam-off period as shown in FIG. 5. If, during the repeated processing of steps 75 to 80, it is determined in step 77 or 80 that a total of the dose value measured by the dose meter has reached the target dose, the processing of step 83 is executed and the irradiation of the ion beam toward the patient 22 is brought to an end.

If the determination result in step 81 is "NO", the processing subsequent to step 73 is executed again. More specifically, if the current density of the ion beam circulating within the synchrotron 4 lowers and the extraction of the ion beam is disabled, the ion beam in the synchrotron 4 is decelerated. The magnet power supply controller reduces the current values supplied to the respective magnets disposed in the synchrotron 4, the beam transportation line 2, etc. The current values supplied to those magnets are held at values corresponding to the state allowing entry of the ion beam. The ion beam is then introduced to the synchrotron 4 from the pre-accelerator 3. The ion beam is accelerated until reaching the extraction energy, as described above. After the end of acceleration of the ion beam, the processing subsequent to step 73 is executed by the irradiation control/determination section 66.

Because the determination in step 77 is made between steps 76 and 78, the extraction of the ion beam can be stopped when a total of the dose value measured by the dose monitor has reached the target dose during the period in which the ion beam passes the rotating RMW 40. It is hence possible to prevent the ion beam from being excessively irradiated to the tumor K. For example, if the determination in step 77 is made "YES" when the opening 46 between the blade 45A and the blade 45B, shown in FIG. 4, is positioned on the beam axis m, the extraction of the ion beam can be stopped immediately. Therefore, the irradiation of the ion beam to the tumor K can be avoided during the period from the time at which the opening 46 is positioned on the beam axis m to the time at which the point 53A corresponding to the second setting value of the rotational angle is positioned on the beam axis m.

In the example of the case b described above, the region from the point 52A to the point 53A, the region from the point 52B to the point 53B, and the region from the point 52C to the point 53C each represent an ion beam passage region in the RMW 40. The region from the point 53A to the point 52B, the region from the point 53B to the point 52C, and the region from the point 53C to the point 52A each represent a region in the RMW 40 where the ion beam does not pass (i.e., an ion beam non-passage region). While the above description is made, by way of example, in connection with the case b, various SOBP widths can be formed by changing, for one unit of the RWM 40, the first setting values of the rotational angle at each of which the beam extraction start signal is to be outputted and the second setting values of the rotational angle at each of which the beam extraction stop signal is to be outputted. While the ion beam passes the opening 46 in each of the "beam-on" periods shown in FIG. 5, the irradiation control/-determination section 66 may execute control such that the ion beam passes the top portion 36 of the blade in each of the "beam-on" periods instead of passing the opening 46. In such a case, for example, the irradiation control/-determination section 66 outputs the beam extraction start signal when the point 53C has reached the position of the beam axis m in FIG. 4, and outputs the beam extraction stop signal when the point 52A has reached the position of the beam axis m in FIG. 4.

With the above-described on/off-control of extraction of the ion beam performed by the irradiation control/-determination section 66, the desired SOBP width decided for the patient 22 according to the treatment plan can be formed at the tumor K.

While the extraction of the ion beam is continued from the irradiation apparatus 16, the driving control section 68 receives respective device status information of the second scatterer device 29, the range adjustment device 30, and the block collimator 33 in real time (or, e.g., at intervals of a certain period). The device status information is detected by sensors (not shown) disposed on those devices. The driving control section 68 reads the device status information from the memory 69 and determines whether the read information matches with corresponding one of the type of the second scatterer, the thickness of the absorber, and the aperture size of the block collimator. If there is a mismatch in any device status information, i.e., if the result of the above determination is "NO", the driving control section 68 outputs the interlock signal to the interlock device 72. In response to the interlock signal, the interlock device 72 opens the on/off switch 10. Accordingly, even with the on/off switch 9 kept in the closed state, the supply of the RF power from the first RF-power supply 8 to the RF knockout electrode 5 is stopped, whereby the extraction of the ion beam from the synchrotron 4 is also stopped. If the above determination result is "YES", the interlock device 72 does not open the on/off switch 10 and therefore the extraction of the ion beam from the synchrotron 4 is continued when the on/off switch 9 is in the closed state.

The irradiation control/determination section 66 determines whether the on/off-timing of the gate signal outputted from the gate signal generator 37 is the desired timing. This process will be described in more detail below. The irradiation control/determination section 66 receives the reference signal and the gate signal both outputted from the gate signal generator 37. While the ion beam is being irradiated to the patient 22, the reference signal and the gate signal are inputted to the irradiation control/-determination section 66 of the irradiation controller 64 in real time (or, e.g., at intervals of a certain period). In response to the inputted reference signal and gate signal, the phase determination circuit 83, the gate determination-1 circuit 84, and the gate determination-2 circuit 85 of the irradiation control/determination section 66 start up their timers and compare respectively the counted time Tp (time corresponding to the phase difference between the whole of the gate signal and the rotation of the RMW 40), T1 (time during which the gate signal is turned off), and T2 (time during which the gate signal is turned on) with the corresponding target values "Tp limit±Etp", "T1 limit±Et1" and "T2 limit±Et2" (including the allowable values), which are stored in the memory 69. If even only one of the times Tp, T1 and T2 is out of the respective allowable ranges, this is regarded as indicating that the gate signal is not turned on/off at the desired timing, and therefore the irradiation control/determination section 66 outputs the beam extraction stop signal to the on/off switch 9. In response to the output of the beam extraction stop signal, the on/off switch 9 is opened and the extraction of the ion beam from the synchrotron 4 is stopped. Further, the irradiation control/determination section 66 outputs the interlock signal (gate phase/gate timing abnormality signal) to the interlock device 72, thereby closing the beam shutter 38. As a result, the extraction of the ion beam from the synchrotron 4 can be stopped with certainty.

On the other hand, if the times Tp, T1 and T2 are all within the respective allowable ranges, this is regarded as indicating that the gate signal is turned on/off at the desired timing, and therefore the irradiation control/determination section 66 allows the output of the beam extraction start signal, as it its, to the on/off switch 9 (namely, it outputs the beam extraction start signal and the beam extraction stop signal as usual). Accordingly, the irradiation of the ion beam to the patient 22 is continued. As described above, the irradiation of the ion beam is continued until the dose measured based on the detection signal from the dose monitor 31 reaches the target dose. The gate phase/gate timing abnormality signal outputted from the irradiation control/determination section 66 is displayed on the display 54. Note that a certain sign indicating the normal state may also be displayed.

With the charged particle beam extraction system 24 of this embodiment, since the on/off-control of the ion beam is performed during the rotation of the RMW 40, the region in the RMW 40 where the ion beam passes the RMW 40 can be varied in the rotating direction of the RMW 40. Accordingly, a plurality of SOBP widths having different values in the direction of depth from the body surface of the patient 22 can be formed by using one RMW 40, and hence one RMW 40 can be used for a plurality of patients. In other words, the number of patients treatable using one RMW 40 is increased. Also, since a plurality of SOBP widths can be formed by using one RMW 40, it is possible to reduce the number of RMWs to be prepared in a cancer therapy center in which the charged particle beam extraction system 24 is installed. Further, since a plurality of SOBP widths can be formed by using one RMW 40, it is possible to reduce the number of times at which the RMW installed in the irradiation apparatus 16 is to be replaced. This is advantageous in cutting the time required for preparations of the treatment and in increasing the number of patients treated by the charged particle beam extraction system 24. Especially, in this embodiment, since the on/off-control of the ion beam is performed depending on the rotational angle (specifically the measured values and the setting values of the rotational angle) of the RMW 40, each particular SOBP width can be formed with high accuracy. By changing the rotational angle of the RMW at which the ion beam is on/off-controlled, the SOBP widths having various values can be formed optionally.

In the synchrotron 4, the number of accelerated ions is constant. Therefore, even when the beam-on period is shortened, the current density of the ion beam extracted from the synchrotron 4 during the beam-on period can be increased by increasing the RF power supplied from the first RF-power supply 8 to the RF knockout electrode 5 for extraction of the ion beam. Hence, the dose rate for irradiation to the patient (i.e., the radiation dose irradiated to the patient per unit time and per unit volume) can be increased even in a short beam-on period. In other words, the irradiation time of the ion beam can be shortened for the patient 22 having the tumor K with a small thickness or a small volume by irradiating the ion beam having the increased current density. This reduction of the irradiation time contributes to reducing the burden imposed on the patient 22 and increasing the number of patients treatable per year. Further, even in the case of shortening the beam-on period, all of the circulating ion beam can be essentially extracted from the synchrotron 4 by increasing the RF power applied for the extraction of the ion beam as mentioned above. As a result, a degree of radiation accumulated in the equipment, such as the synchrotron 4, can be reduced.

A cyclotron may also be used as an accelerator instead of the synchrotron, and an ion beam extracted from the cyclotron may be introduced to the irradiation apparatus 16. However, the cyclotron does not include the decelerating step unlike the synchrotron, and performs steps of entering, accelerating and extracting the ion beam in succession. Accordingly, if the "beam-on" period is shortened, the number of ions extracted from the irradiation apparatus 16 per unit time is reduced, while the rate of dose irradiated to the tumor K is not changed. This results in a reduction of the SOBP width and is hence equivalent to a reduction of the volume subjected to the irradiation. As a result, even when the "beam-on" period is shortened, the irradiation time of the ion beam is not changed for the patient 22 having the tumor K with a small thickness or a small volume. If the extraction of the ion beam is turned off during or after the step of accelerating the ion beam in the cyclotron, the amount of the ion beam discarded is increased and a degree of radiation accumulated in the equipment, such as the cyclotron, is increased.

With the charged particle beam extraction system 24 of this embodiment, whether the turning-on/off of the gate signal from the gate signal generator 37, i.e., the turning-on/off of the beam extraction from the synchrotron 4, is performed at the desired timing can be confirmed in real time during the irradiation of the ion beam. When the turning-on/off of the gate signal is not performed at the desired timing, the extraction of the ion beam can be stopped. It is therefore possible to prevent an abnormal SOBP width, which differs from the SOBP width set in the treatment plan, from being formed in the body of the patient 22. Consequently, safety in the treatment using the ion beam can be significantly increased. Further, according to this embodiment, when the turning-on/off of the gate signal is not performed at the desired timing, the beam shutter 38 is also closed in addition to stop of the extraction of the ion beam. As a result, the extraction of the ion beam from the synchrotron 4 can be stopped with certainty. Thus, since the means for stopping the ion beam in the event of an abnormality is provided double, this embodiment is able to reliably avoid the ion beam from being erroneously irradiated to the patient and to ensure higher safety.

Moreover, according to this embodiment, in the case of no abnormality in the detected device status information regarding the first scatterer, the second scatterer device 29, and the range adjustment device 30, when the turning-on/off of the gate signal, i.e., the turning-on/off of the beam extraction from the synchrotron 4, is performed at the desired timing, this means, as described above, that the desired SOBP width is formed. In the case of the device status information being normal, therefore, this embodiment makes it possible to confirm in real time during the irradiation of the ion beam whether the actual SOBP width formed in accordance with the beam on/off-control performed on the RMW 40 is equal to the desired setting value of the SOBP width.

Still further, according to this embodiment, since the gate phase/gate timing abnormality signal outputted from the irradiation control/determination section 66 is displayed on the display 54, a doctor (or a radiation engineer) is able to confirm an abnormality in the beam on/off-timing (i.e., an abnormality of the SOBP width formed in the body of the patient 22). Therefore, in the event that the extraction of the ion beam from the synchrotron 4 is not stopped with an abnormality occurred in the interlock device 72, etc. in spite of an gate phase/gate timing abnormality being displayed on the display 54, the doctor (or the radiation engineer) is able to open the on/off switch 10 by depressing a beam extraction stop button disposed on an operator condole (not shown) in the control room. In other words, the extraction of the ion beam from the synchrotron 4 can be manually stopped.

Second Embodiment

A charged particle beam extraction system according to another embodiment of the present invention will be described below with reference to FIGS. 11 and 12. In the charged particle beam extraction system of this second embodiment, the irradiation control/determination section 66 of the irradiation controller 64 in the above-described first embodiment, which measures the times Tp, T1 and T2 by using the timers, is replaced by an irradiation control/determination section (determination unit and third control unit) 66A which utilizes internal or external clocks and measures the times Tp, T1 and T2 by counting the internal or external clocks.

Figure 11:
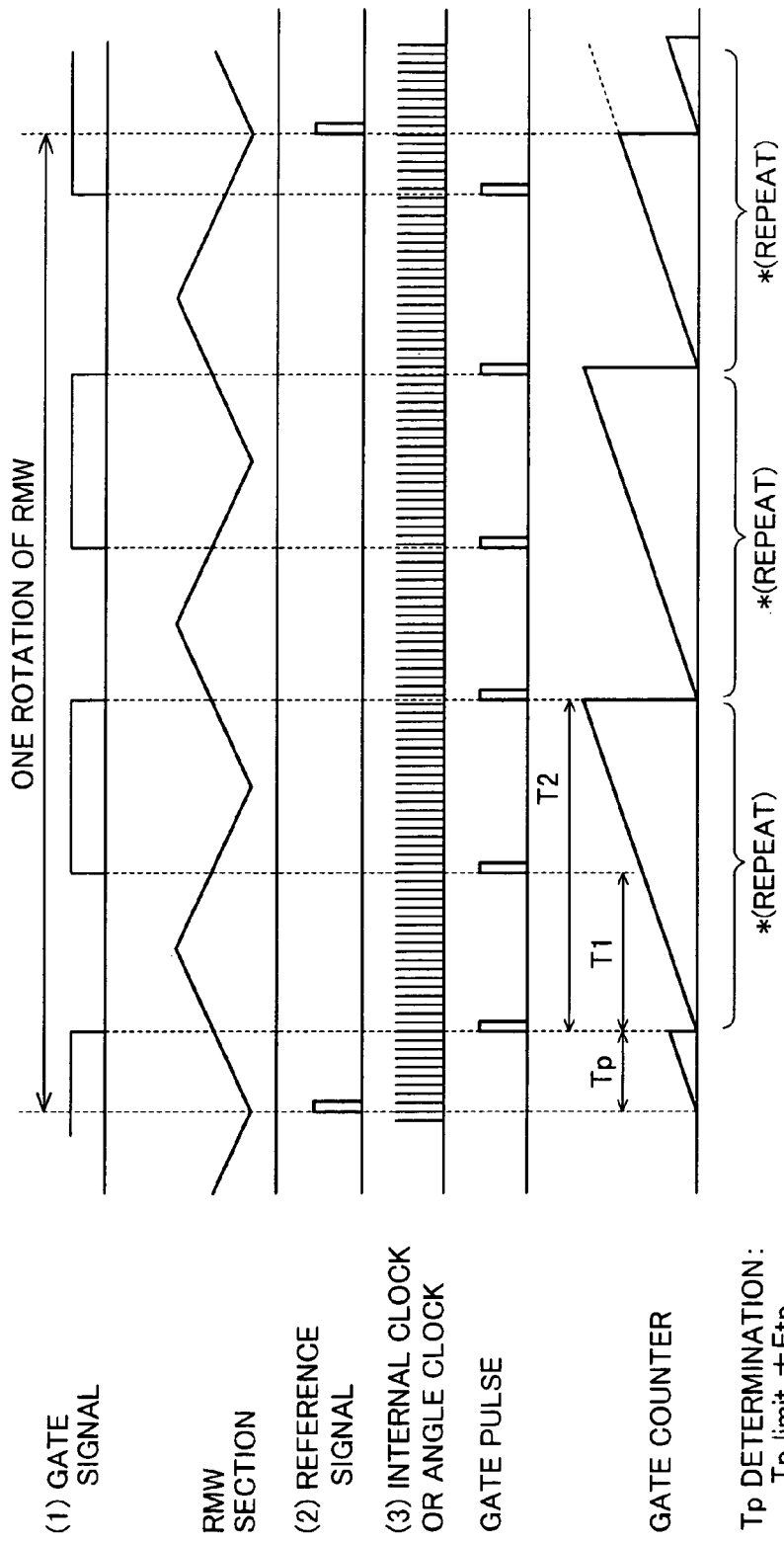
FIG. 11 is a time chart showing the relationship between rotation of the RMW and a gate signal in a second embodiment of the present invention.
Figure 12:
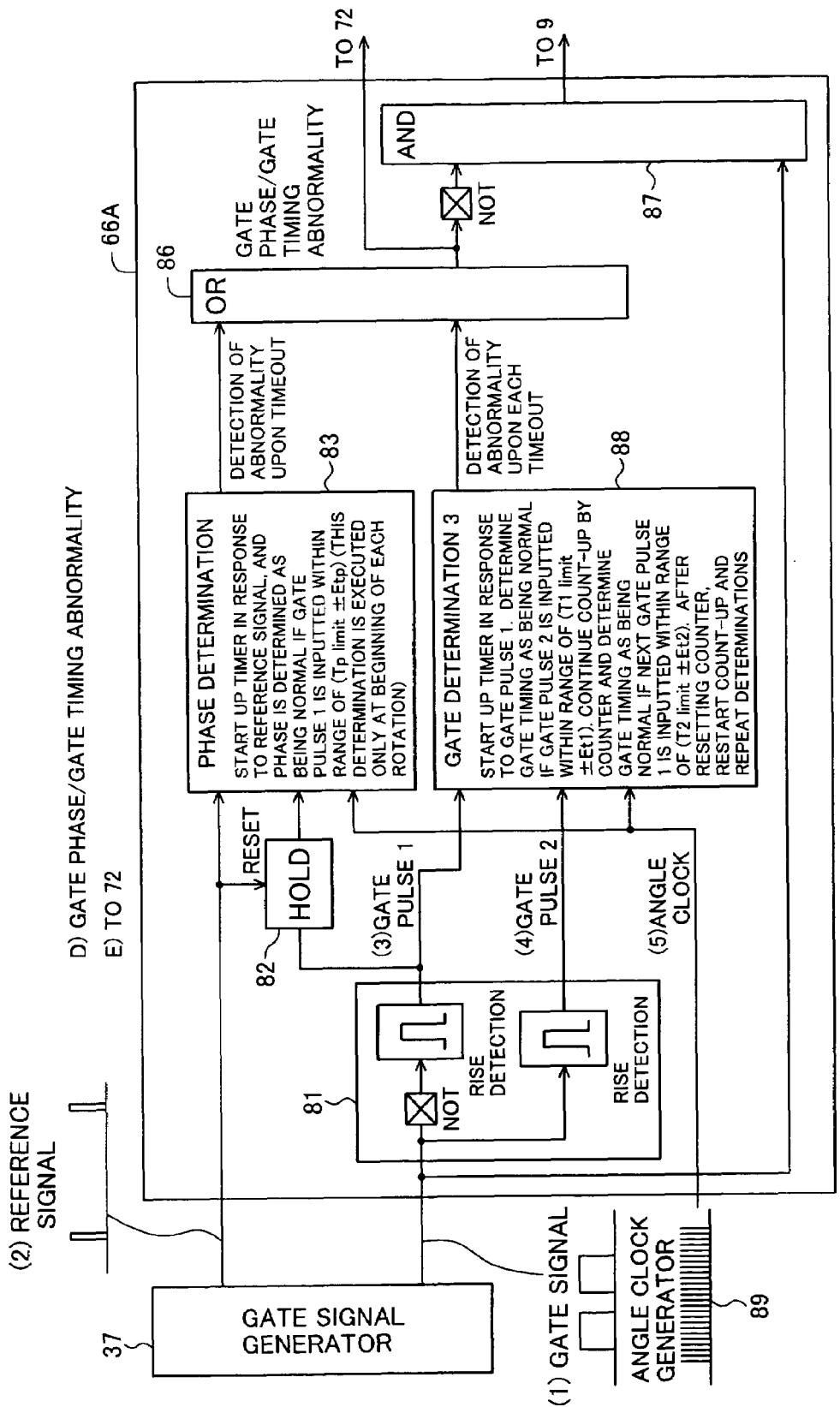
FIG. 12 is a functional block diagram showing the determining function of an irradiation control/determination section in the second embodiment of the present invention.

FIG. 11 is a time chart showing the relationship between the rotation of the RMW 40 and the gate signal in this second embodiment, and FIG. 12 is a functional block diagram showing the determining function of the irradiation control/determination section 66A. In FIGS. 11 and 12, similar components to those in FIGS. 7 and 8 are denoted by the same symbols and a description of those components is omitted here.

As shown in FIGS. 11 and 12, this second embodiment employs internal clocks or angle clocks for determining the gate phase and the gate timing. Each clock provides a time unit for use in making the determination. More specifically, the internal clocks serve as clock signals generated by a clock generator (e.g., a quartz oscillator) incorporated in the irradiation controller 64A itself. On the other hand, the angle clocks serve as pulse signals generated, for example, in sync with the rotation of the RMW 40 provided in the irradiation apparatus 16. As a matter of course, it is also possible to make the determinations by counting the internal clocks without using the angle clocks. In such a case, the angle clocks are not required. However, the use of the angle clocks is advantageous in that, if the rotation speed of the RMW 40 should be changed, the gate signal can be determined using the clocks generated in sync with the rotation of the RMW 40 and correct determination can be resulted without being affected by change in the rotation speed of the RMW 40. Therefore, the following description is made of the case where an angle clock generator (clock generator, e.g., an encoder) 89 is provided and the angle clocks are used.

As shown in FIG. 12, the gate signal (denoted by (1) in FIG. 12) and the reference signal (denoted by (2) in FIG. 12) are inputted to the irradiation control/determination section 66A from the gate signal generator 37. The reference signal inputted from the gate signal generator 37 is, as in the above-described first embodiment, applied to a phase determination circuit 83, whereupon the phase determination circuit 83 starts up a not-shown counter (counting unit) to start counting of the angle clocks (denoted by (5) in FIG. 12) inputted from the angle clock generator 89. Also, the inputted gate signal is, as in the above-described first embodiment, applied to an input processing circuit 81 where a rise or a fall of the gate signal is detected. When a fall of the gate signal is detected, a gate pulse-1 signal (denoted by (3) in FIG. 12) is inputted from the input processing circuit 81, via a hold circuit 82, to the phase determination circuit 83 where Tp determination is executed in the same manner as the process using the above-described equation (i).

The gate pulse-1 signal (denoted by (3) in FIG. 12) from the input processing circuit 81 is further inputted to a gate determination-3 circuit 88. Responsively, the gate determination-3 circuit 88 starts up a not-shown counter to start counting of the angle clocks (denoted by (5) in FIG. 12) inputted from the angle clock generator 89. Then, when a rise of the gate signal is detected, a gate pulse-2 signal (denoted by (4) in FIG. 12) is inputted from the input processing circuit 81 to the gate determination-3 circuit 88 where T1 determination is executed in the same manner as the process using the above-described equation (ii). Thereafter, the counter continues the count-up, and when a fall of the gate signal is detected again, the gate pulse-1 signal (denoted by (3) in FIG. 12) is inputted from the input processing circuit 81 to the gate determination-3 circuit 88 where T2 determination is executed in the same manner as the process using the above-described equation (iii). Thus, the gate determination-3 circuit 88 makes the determinations by comparing the time T1 during which the gate signal is turned off and the time T2 during which the gate signal is turned off and on with respective target values (see FIG. 11 as well).

If the determination is not satisfied in any of the determination circuits 83 and 88, a signal indicating detection of an abnormality is inputted to an OR circuit 86 which produces a gate phase/gate timing abnormality signal, as in the above-described first embodiment. This abnormality signal is applied to a succeeding AND circuit 87 via a NOT circuit. With such an arrangement, the AND circuit 87 provides the beam extraction start signal or the beam extraction stop signal to the on/off switch 9 only when the gate timing is normal, whereby the on/off-control of the beam extraction can be performed. Thus, if an abnormality of the gate timing is detected in any of the determination circuits 83 and 88, the output of the gate signal to the on/off switch 9 is turned off (namely, the beam extraction stop signal is outputted to the on/off switch 9). As a result, the on/off switch 9 is opened and the beam extraction from the synchrotron 4 is stopped. At the same time, the interlock signal is outputted to the interlock device 72, whereupon the interlock device 72 closes the beam shutter 38 to prevent the ion beam from being transported toward the irradiation apparatus 16.

According to this second embodiment, since the angle clocks in sync with the rotation of the RMW 40 are used in the phase and time determinations for the gate timing, the determinations can be correctly made with no need of compensations or the like even if the rotation of the RMW 40 should be changed. Further, according to this second embodiment, since the gate determination-3 circuit 88 executes the gate time determination for each blade through the steps of continuously counting the clocks by one counter and comparing the counted value with the target value corresponding to the gate pulse position, the number of counters required for the determinations can be reduced. In the case of providing the counters in number as usual (i.e., the same number as that of the timers used in the first embodiment), therefore, the determinations can be made in a finer manner because the gate determination-3 circuit 88 is able to handle a larger number of gate pulses than two handled in this embodiment.

Third Embodiment

A charged particle beam extraction system according to still another embodiment of the present invention will be described below with reference to FIGS. 13 through 15. In the charged particle beam extraction system of this third embodiment, the irradiation control/determination sections 66, 66A of the irradiation controllers 64, 64A in the above-described first and second embodiments, which measure the times Tp, T1 and T2 by using the timers or the counter and comparing the measured values with the target values to make the determinations, is replaced by an irradiation control/determination section (determination unit and third control unit) 66B which executes the comparisons and the determinations by using memory data having addresses capable of being updated. Further, another gate signal generator is additionally provided.

Figure 13:
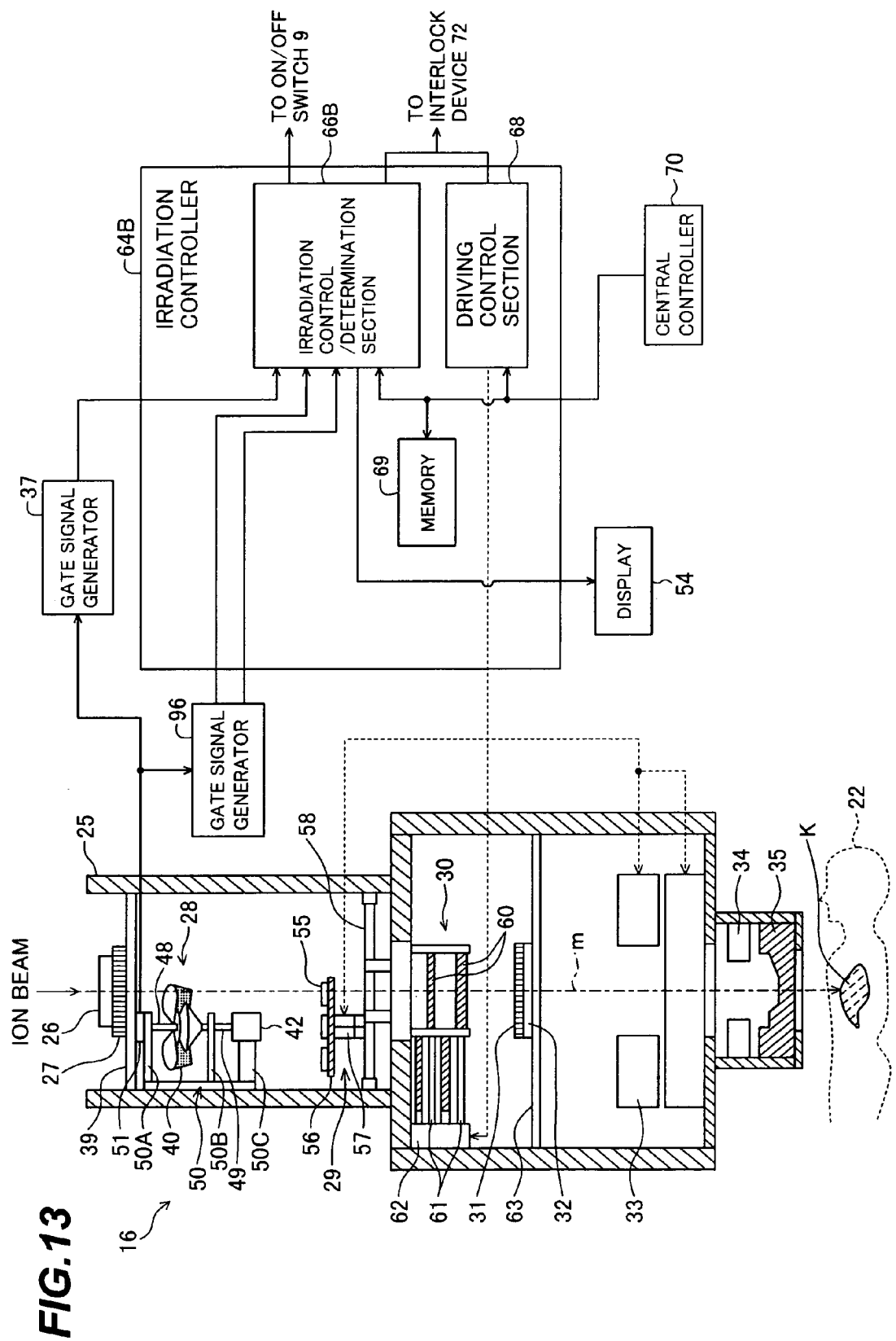
FIG. 13 is a vertical sectional view showing a detailed structure of an irradiation apparatus in a third embodiment of the present invention.

FIG. 13 is a vertical sectional view showing a detailed structure of an irradiation apparatus in a charged particle beam extraction system according to this third embodiment. In FIG. 13, similar components to those in FIG. 2 are denoted by the same symbols and a description of those components is omitted here.

As shown in FIG. 13, the charged particle beam extraction system according to this third embodiment includes another gate signal generator (second control unit) 96 in addition to the gate signal generator 37. As with the gate signal generator 37, the gate signal generator 96 generates and outputs the reference signal depending on the rotational angle of the RMW 40, which is inputted from the angle meter 51, and also outputs, as the angle clock, an encoder output pulse, which is outputted from an encoder (not shown) associated with the angle meter 51, to an irradiation control/determination section 66B.

Figure 14:
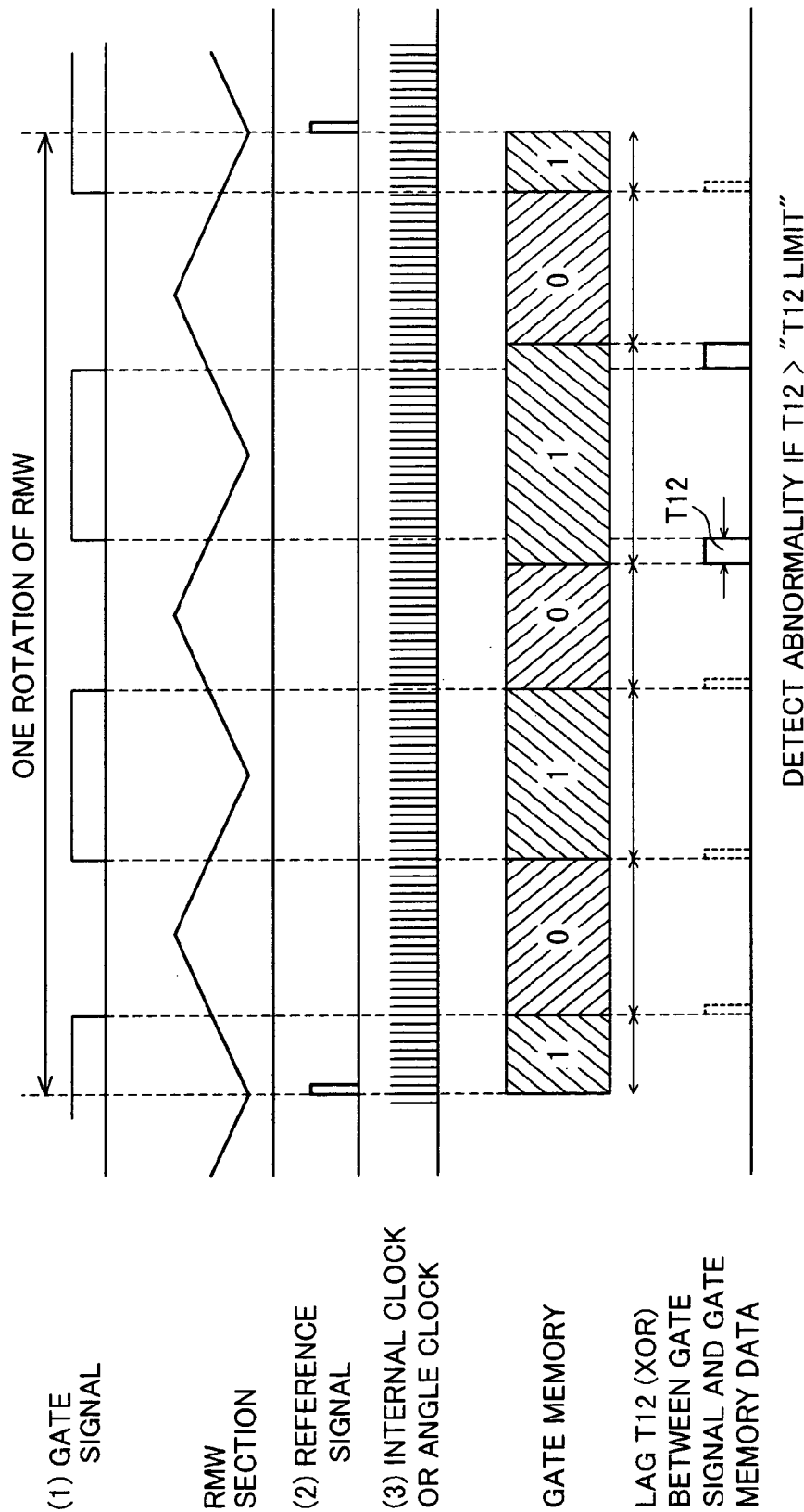
FIG. 14 is a time chart showing the relationship among rotation of the RMW, a gate signal, and a gate memory in the third embodiment of the present invention.
Figure 15:
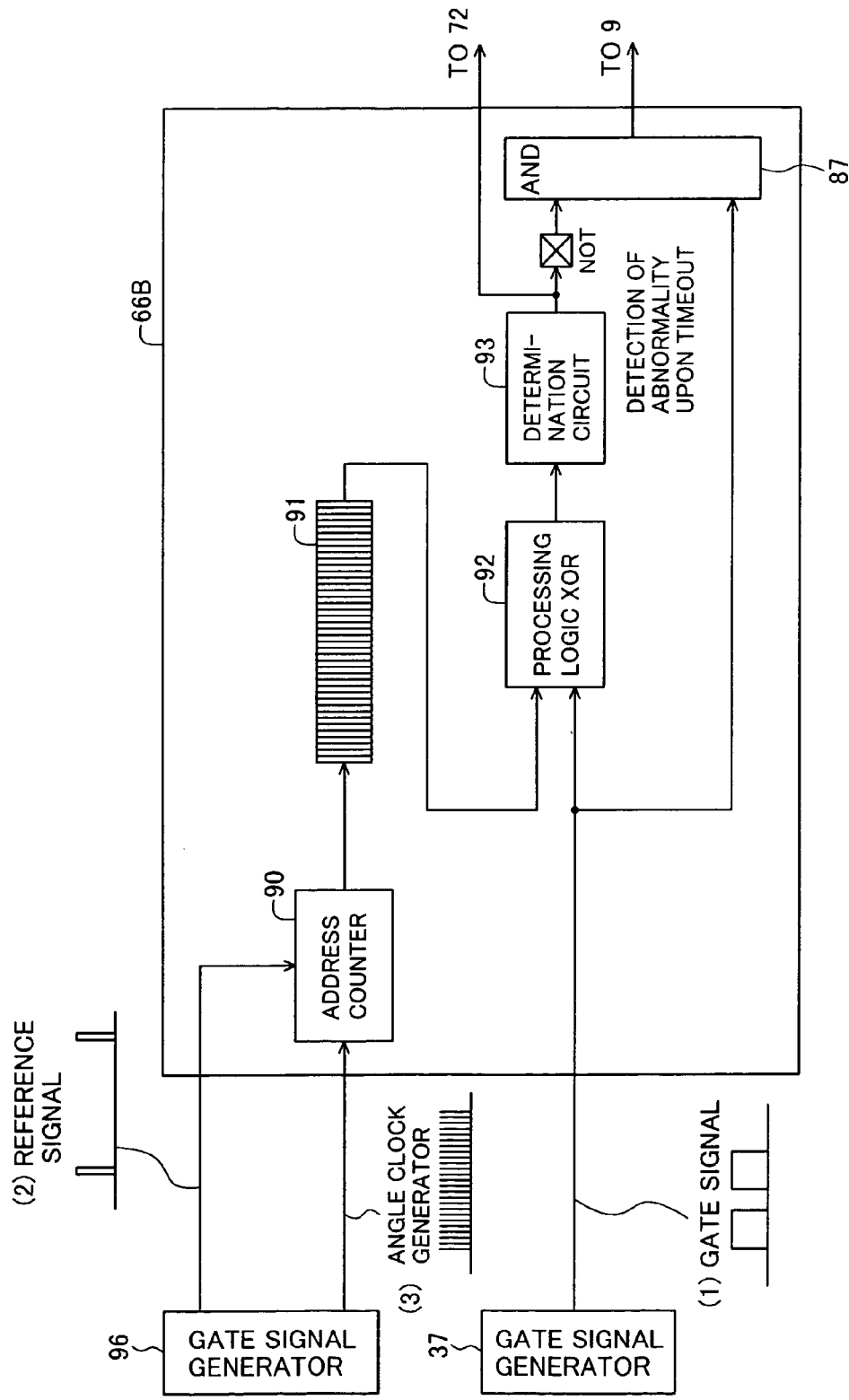
FIG. 15 is a functional block diagram showing the determining function of an irradiation control/determination section shown in FIG. 13.

FIG. 14 is a time chart showing the relationship among the rotation of the RMW 40, the gate signal, and a gate memory in this third embodiment, and FIG. 15 is a functional block diagram showing the determining function of the irradiation control/determination section 66B. In FIGS. 14 and 15, similar components to those in FIGS. 7 and 8 or FIGS. 11 and 12 are denoted by the same symbols and a description of those components is omitted here.

In this third embodiment, as shown in FIG. 14, instead of making the determinations on the gate signal by using the timers or the counter as described above, a gate signal comparing process is performed by using memory data that is stored in a gate memory incorporated in the irradiation control/determination section 66B. The address of the gate memory can be updated just in sync with the internal clock or the angle clock. The angle clock inputted from the gate signal generator 96 is employed herein. The gate memory stores data corresponding to the on/off-state of the gate signal. In this third embodiment, by way of example, data "1" is written in the gate memory for a period during which the gate signal should be kept in the on-state, and data "0" is written in the gate memory for a period during which the gate signal should be kept in the off-state. The address is reset in response to the reference signal per rotation of the RMW 40.

Referring to FIG. 15, an address counter 90 counts the angle clocks (denoted by (3) in FIG. 15) inputted from the gate signal generator 96, and designates the address of a gate memory (storage) 91. Also, the address counter 90 is reset by the reference signal (denoted by (2) in FIG. 15) and repeats the operation per rotation of the RMW 40. The data in the gate memory 91 is inputted to a processing logic 92. On the other hand, the gate signal (denoted by (1) in FIG. 15) outputted from the gate signal generator 37 is also inputted to the processing logic 92. The processing logic 92 takes the exclusive logical sum (XOR) between the gate signal from the gate signal generator 37 and data read out of the gate memory 91. T12 (see FIG. 14) resulting from the XOR processing represents a lag between the gate signal and the read-out data. A determination circuit 93 determines the magnitude of the lag T12. If the magnitude of the lag T12 exceeds a limit value ("T12 limit") (i.e., T12>"T12 limit"), this is determined as indicating the occurrence of an abnormality, and the interlock signal is outputted to the interlock device 72. In this case, the beam extraction stop signal is outputted to the on/off switch 9, whereby the beam extraction from the synchrotron 4 is stopped. Further, the interlock device 72 closes the beam shutter 38 to prevent the ion beam from being transported toward the irradiation apparatus 16.

According to this third embodiment, since the soundness of the original gate signal (from the gate signal generator 37) is determined by using the angle clock from the gate signal generator 96 instead of the gate signal from it, the safety of the system can be stepped up without increasing the number of required gate signal generators each of which generally has a complicated structure because of comprising, e.g., a resolver and a magnetic encoder.

Fourth Embodiment

A charged particle beam extraction system according to still another embodiment of the present invention will be described below with reference to FIG. 16. In the charged particle beam extraction system of this fourth embodiment, another gate signal generator is additionally provided as in the above-described third embodiment. Further, the irradiation control/determination section 66 of the irradiation controllers 64 in the above-described first embodiment is replaced by an irradiation control/-determination section (determination unit and third control unit) 66C which compares the gate signals from the two gate signal generators, as they are, for determination of the gate timing.

Figure 16:
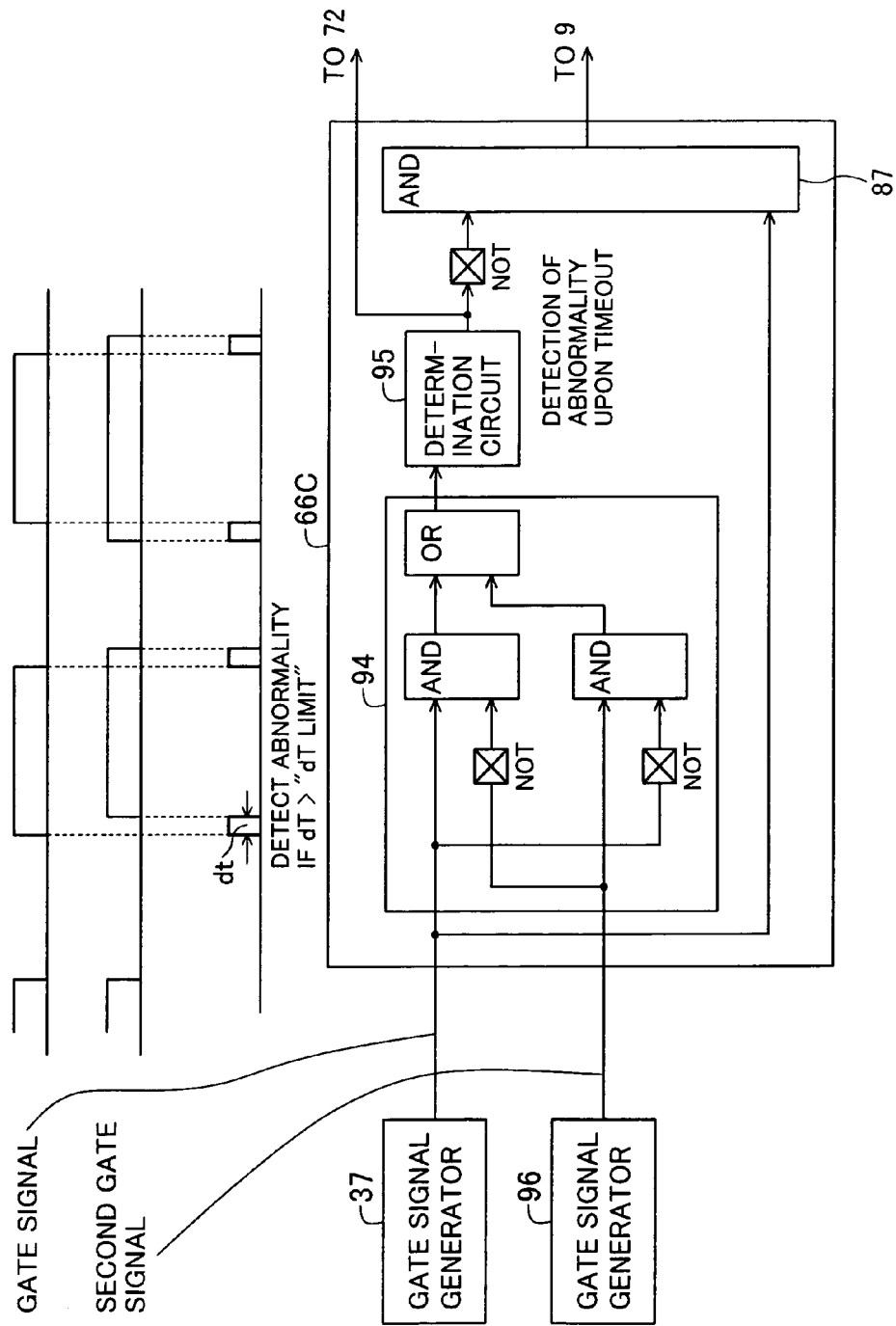
FIG. 16 is a functional block diagram showing the determining function of an irradiation control/determination section in a fourth embodiment of the present invention.

FIG. 16 is a functional block diagram showing the determining function of the irradiation control/-determination section 66C in this fourth embodiment. In FIG. 16, similar components to those in FIG. 15, etc. are denoted by the same symbols and a description of those components is omitted here.

In this fourth embodiment, as shown in FIG. 16, the gate signal outputted from the gate signal generator 37 and the gate signal (second control signal) from the gate signal generator 96 are inputted, as they are, to a processing logic 94 that takes the exclusive logical sum of both the inputs. A lag dT between those two gate signals is thereby detected. Then, a determination circuit 95 determines whether the lag dT exceeds a determination allowable value "dT limit" (i.e., dT>"dT limit"). If the lag dT exceeds the determination allowable value "dT limit", this is determined as indicating the occurrence of an abnormality, and the interlock signal is outputted to the interlock device 72. In this case, the beam extraction stop signal is outputted to the on/off switch 9, whereby the beam extraction from the synchrotron 4 is stopped. Further, the interlock device 72 closes the beam shutter 38 to prevent the ion beam from being transported toward the irradiation apparatus 16.

According to this fourth embodiment, there is no need of measuring the gate timing for each of the two gate signals to make the determination, and the gate timing can be determined for each blade of the RMW 40 based on only the lag between the two gate signals. It is therefore possible to simplify the determination process.

In the above description, the process for generating the gate signal by using the angle meter 51 and the gate signal generator 37 or 96 comprises the steps of counting the encoder output pulses outputted from the encoder associated with the angle meter 51, which is rotated in sync with the rotation of the RMW 40, and turning on or off the gate signal when the count value of the encoder output pulses matches with the target count value which corresponds to the gate on/off-timing and is stored beforehand. However, the process for generating the gate signal is not limited to such an example. For example, a resolver may be used in place of the encoder. The resolver comprises a stator coil and a rotating coil, and it generates a sine wave output having a phase that is lagged relative to a reference sine wave with rotation. Such a resolver may be incorporated in the angle meter 51 (or disposed near the RMW 40) so that the gate signal is generated based on an output of the resolver. Further, the gate signal may be generated by machining an outer circumferential surface of, e.g., the RMW 40 or the rotary shaft 48, 49 in such a way as to provide magnetic, mechanical or optical cyclic changes, obtaining rotation information in the form of rotation pulses with the aid of an appropriate sensor, and counting the rotation pulses.

What is claimed is:

1. A charged particle beam extraction system for extracting a charged particle beam toward an irradiation target, the system comprising:
    a charged particle beam generator for generating the charged particle beam;
    an irradiation apparatus including a wheel having a thickness varied in the direction of travel of the charged particle beam extracted from said charged particle beam generator such that energy of the charged particle beam passing said wheel is changed to form a spread-out Bragg peak width in said irradiation target, said irradiation apparatus irradiating the charged particle beam having passed said wheel toward said irradiation target;
    a first control unit for controlling start and stop of extraction of the charged particle beam from said charged particle beam generator in accordance with a rotational angle of said wheel; and
    a determination unit for determining whether the start and stop of extraction of the charged particle beam is controlled at a desired timing by said first control unit.

2. The charged particle beam extraction system according to claim 1, wherein said first control unit controls the start and stop of extraction of the charged particle beam from said charged particle beam generator by turning on/off output of a first control signal in accordance with the rotational angle of said wheel.

3. The charged particle beam extraction system according to claim 2, wherein said determination unit determines whether the start and stop of extraction of the charged particle beam is controlled at the desired timing by said first control unit, by comparing on/off-timings of the output of the first control signal with respective target values of the on/off-timings.

4. The charged particle beam extraction system according to claim 2, further comprising a second control for turning on/off output of a second control signal in accordance with the rotational angle of said wheel.

5. The charged particle beam extraction system according to claim 4, wherein said determination unit determines whether the start and stop of extraction of the charged particle beam is controlled at the desired timing, by comparing the first control signal with the second control signal.

6. The charged particle beam extraction system according to claim 4, further comprising a storage for updating an address in accordance with turning-on/off of the second control signal, wherein said determination unit determines whether the start and stop of extraction of the charged particle beam is controlled at the desired timing, by comparing the address of said storage with the first control signal.

7. The charged particle beam extraction system according to claim 1, 3, 5 or 6, further comprising a third control unit for controlling said charged particle beam generator to stop extraction of the charged particle beam when said determination unit determines that the start and stop of extraction of the charged particle beam is not controlled at the desired timing.

8. The charged particle beam extraction system according to claim 3, further comprising a timer unit for measuring the on/off-timing of output of the first control signal.

9. The charged particle beam extraction system according to claim 3, further comprising a clock generator for generating clocks, and a counting unit for measuring the on/off-timing of output of the first control signal by counting the clocks generated from said clock generator.

10. The charged particle beam extraction system according to claim 9, wherein said clock generator is disposed in said determination unit and generates the clocks at a predetermined time cycle.

11. The charged particle beam extraction system according to claim 9, wherein said clock generator generates the clocks in sync with rotation of said wheel.

12. The charged particle beam extraction system according to claim 1, wherein said charged particle beam generator includes a synchrotron.

13. The charged particle beam extraction system according to claim 7, wherein said charged particle beam generator includes a synchrotron having an RF knockout electrode, and said third control unit stops application of an RF wave to said RF knockout electrode to stop extraction of the charged particle beam from said synchrotron when said determination unit determines that the start and stop of extraction of the charged particle beam is not controlled at the desired timing.

14. The charged particle beam extraction system according to claim 13, wherein said first control unit controls the start and stop of extraction of the charged particle beam by respectively starting and stopping supply of the RF wave to said RF knockout electrode.

15. A charged particle beam extraction method for allowing a charged particle beam extracted from a charged particle beam generator to be irradiated from an irradiation apparatus including a wheel having a thickness varied in the direction of travel of the charged particle beam such that energy of the charged particle beam passing said wheel to form a spread-out Bragg peak width in an irradiation target, the method comprising the steps of:
    controlling start and stop of extraction of the charged particle beam from said charged particle beam generator in accordance with a rotational angle of said wheel; and
    determining whether the start and stop of extraction of the charged particle beam is controlled at desired timing.

16. The charged particle beam extraction method according to claim 15, wherein the start and stop of extraction of the charged particle beam from said charged particle beam generator is controlled by turning on/off output of a first control signal in accordance with the rotational angle of said wheel.

17. The charged particle beam extraction method according to claim 16, wherein whether the start and stop of extraction of the charged particle beam is controlled at the desired timing is determined by comparing on/off-timings of the output of the first control signal with respective target values of the on/off-timings.

18. The charged particle beam extraction method according to claim 16, further comprising the step of turning on/off output of a second control signal in accordance with the rotational angle of said wheel.

19. The charged particle beam extraction method according to claim 18, wherein whether the start and stop of extraction of the charged particle beam is controlled at the desired timing is determined by comparing the first control signal with the second control signal.

20. The charged particle beam extraction method according to claim 18, wherein whether the start and stop of extraction of the charged particle beam is controlled at the desired timing is determined by comparing the first control signal with an address updated in accordance with turning-on/off of the second control signal.

21. The charged particle beam extraction method according to claim 15, 17, 19 or 20, further comprising the step of stopping the extraction of the charged particle beam when the determination shows that the start and stop of extraction of the charged particle beam is not controlled at the desired timing.

22. The charged particle beam extraction system according to claim 7, further comprising:
a beam transportation line associated with said charged particle beam generator for transporting the charged particle beam extracted therefrom; and
a beam shutter disposed in said beam transportation line; and
wherein said third control unit controls said beam shutter to close while controlling said charged particle beam generator to stop extraction of the charged particle beam when said determination unit determines that the start and stop of extraction of the charged particle beam is not controlled at the desired timing.

23. The charged particle beam extraction system according to claim 7,
wherein said charged particle beam generator includes a synchrotron, an RF knockout electrode disposed in the synchrotron for applying an RF wave to the charged particle beam circulating in said synchrotron, and a RF-power supply for supplying the RF wave to said RF knockout electrode through an on/off switch, and wherein said first control unit controls start and stop of extraction of the charged particle beam from said charged particle beam generator by controlling opening and closing of said on/off switch in accordance with a rotational angle of said wheel thereby to control starting and stopping of supply of the RF wave to said RF knockout electrode, and said third control unit controls said charged particle beam generator to stop extraction of the charged particle beam by opening said on/off switch thereby to stop supply of the RF wave to said RF knockout electrode when said determination unit determines that the start and stop of extraction of the charged particle beam is not controlled at the desired timing.

24. The charged particle beam extraction method according to claim 21,
wherein a beam shutter is disposed in a beam transportation line associated with said charged particle beam generator for transporting the charged particle beam extracted therefrom, and said beam shutter is controlled to close while said charged particle beam generator is controlled to stop extraction of the charged particle beam when said determination unit determines that the start and stop of extraction of the charged particle beam is not controlled at the desired timing.

25. The charged particle beam extraction method according to claim 21,
wherein said charged particle beam generator includes a synchrotron, an RF knockout electrode disposed in the synchrotron for applying an RF wave to the charged particle beam circulating in said synchrotron, and a RF-power supply for supplying the RF wave to said RF knockout electrode through an on/off switch, and
wherein the start and stop of extraction of the charged particle beam from said charged particle beam generator is controlled by controlling opening and closing of said on/off switch in accordance with a rotational angle of said wheel thereby to control starting and stopping of supply of the RF wave to said RF knockout electrode, ar.d
the extraction of the charged particle beam is stopped by opening said on/off switch thereby to stop supply of the RF wave to said RF knockout electrode when said determination unit determines that the start and stop of extraction of the charged particle beam is not controlled at the desired timing.

* * * * *